(12) United States Patent
Liu

(10) Patent No.: US 11,096,779 B2
(45) Date of Patent: Aug. 24, 2021

(54) IOL INJECTOR HAVING A SPRING-ASSISTED IOL DELIVERY MECHANISM

(71) Applicant: Alcon Inc., Fribourg (CH)

(72) Inventor: Jian Liu, Keller, TX (US)

(73) Assignee: Alcon Inc.

( * ) Notice: Subject to any disclaimer, the term of this patent is extended or adjusted under 35 U.S.C. 154(b) by 165 days.

(21) Appl. No.: 16/454,466

(22) Filed: Jun. 27, 2019

(65) Prior Publication Data

US 2020/0197158 A1    Jun. 25, 2020

Related U.S. Application Data

(60) Provisional application No. 62/781,719, filed on Dec. 19, 2018.

(51) Int. Cl.
*A61F 2/16* (2006.01)

(52) U.S. Cl.
CPC ............ *A61F 2/167* (2013.01); *A61F 2/1678* (2013.01); *A61F 2002/1683* (2013.01)

(58) Field of Classification Search
CPC ...... A61F 2/167; A61F 2/1678; A61F 2/1662; A61F 2/1667; A61F 2/1672; A61F 2/1675; A61F 2/1691; A61F 2/1664; A61F 2002/1683; A61F 2002/1681; A61F 2002/1682; A61F 2002/16903; A61F 2002/16905; A61F 2002/169051; A61F 2002/169053
See application file for complete search history.

(56) References Cited

U.S. PATENT DOCUMENTS

| 2,472,116 | A | 6/1949 | Maynes |
| 6,074,397 | A | 6/2000 | Chambers et al. |
| 2004/0147938 | A1 | 7/2004 | Dusek |
| 2014/0257317 | A1* | 9/2014 | Safabash ............... A61F 2/1678 606/107 |

FOREIGN PATENT DOCUMENTS

| EP | 2340786 A1 | 12/1899 |
| WO | 2010039841 A1 | 4/2010 |

* cited by examiner

*Primary Examiner* — Erich G Herbermann

(57) ABSTRACT

An IOL injector including a plunger having a spring-assisted IOL delivery mechanism is described.

16 Claims, 18 Drawing Sheets

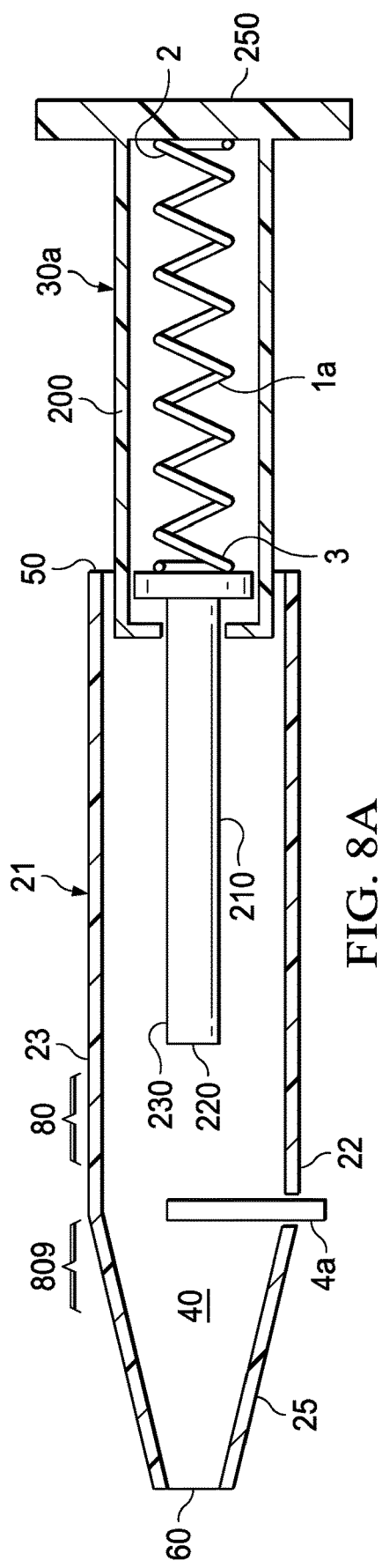
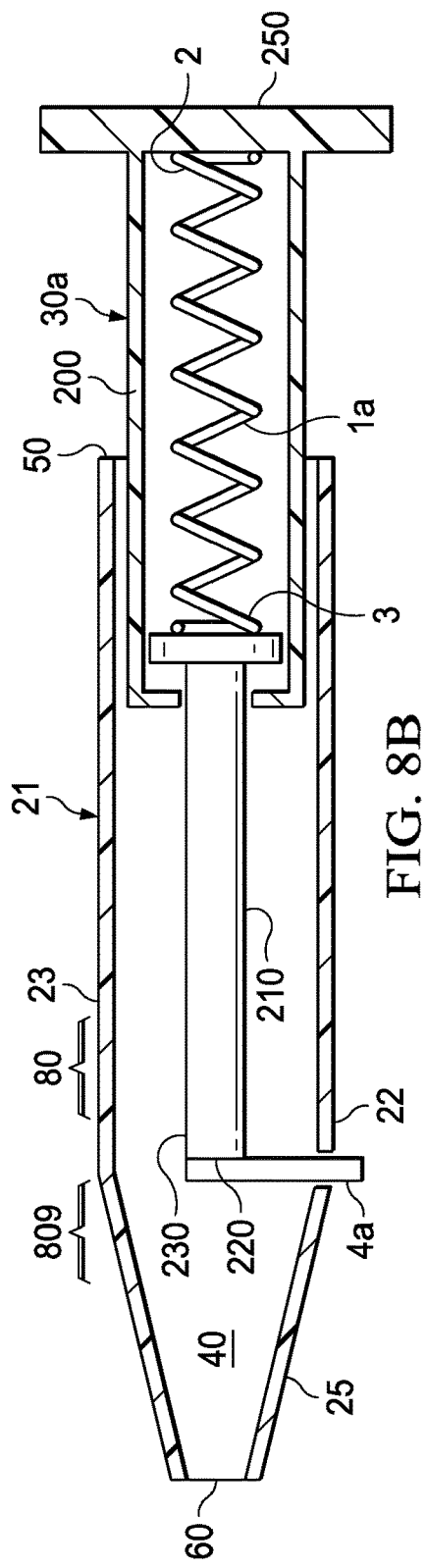
FIG. 8A
FIG. 8B

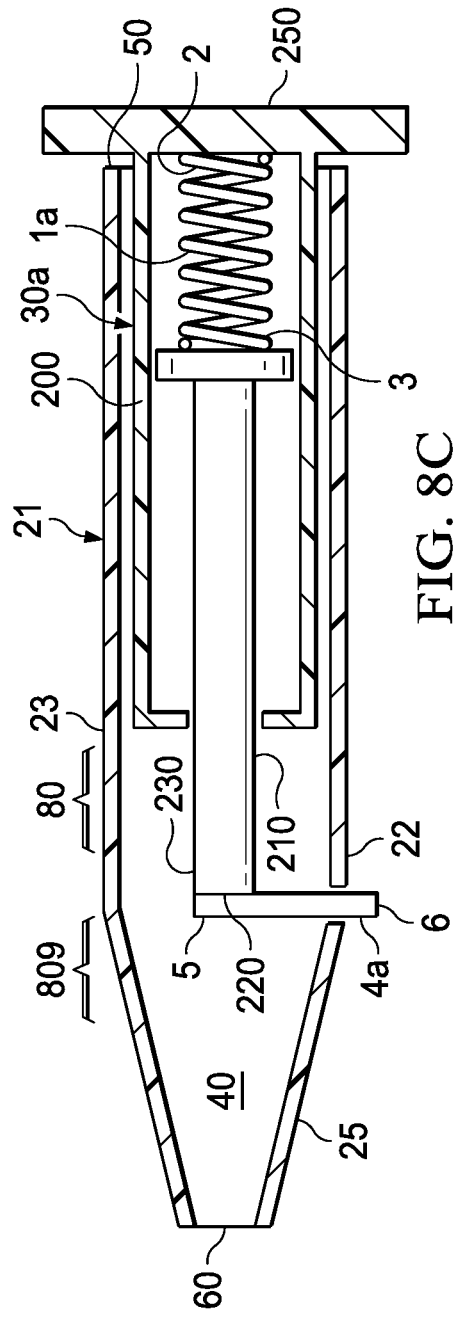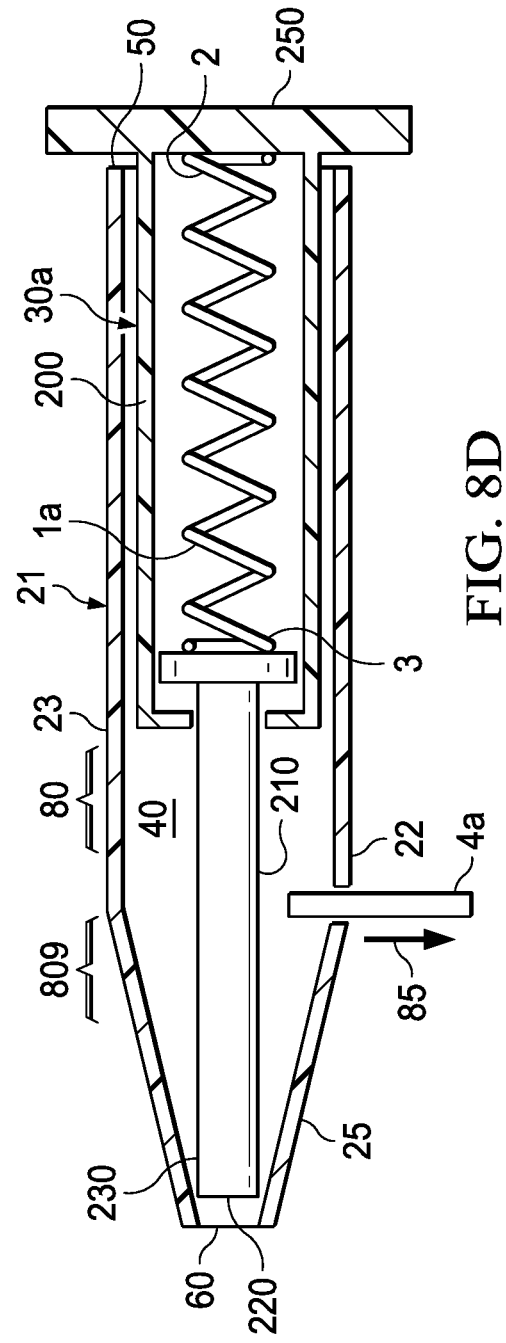

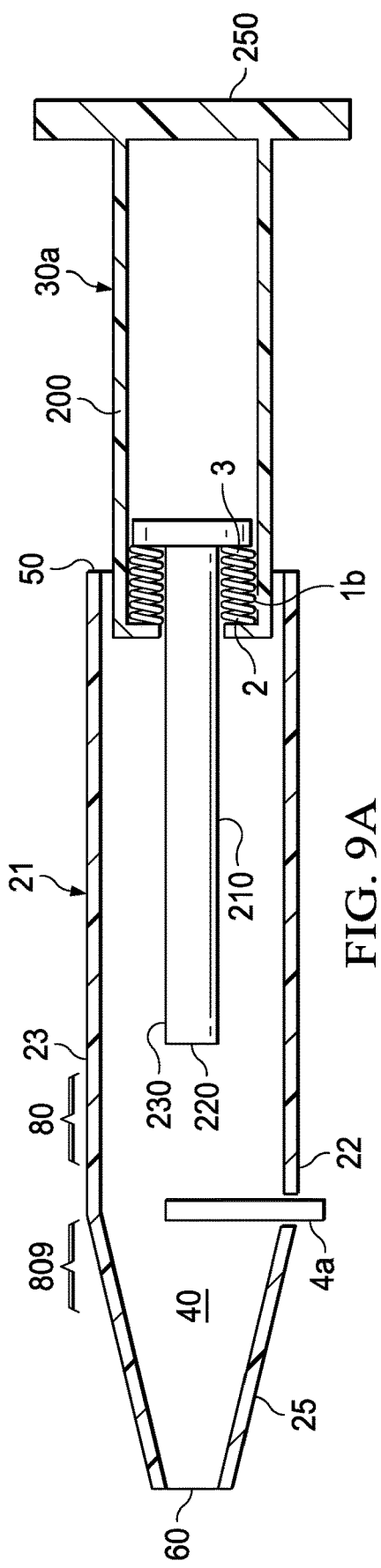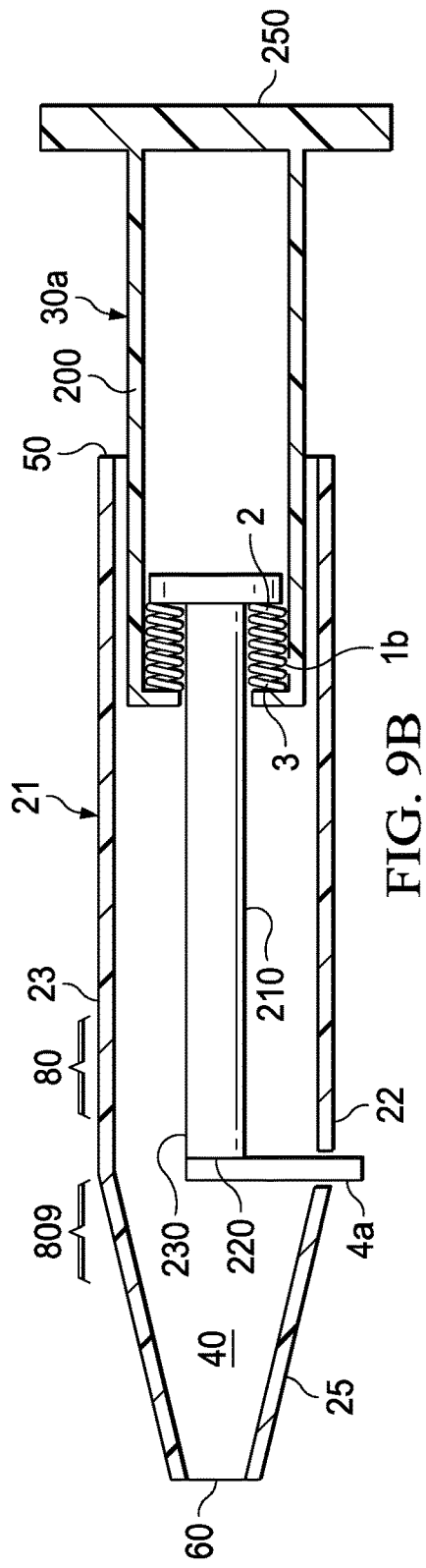

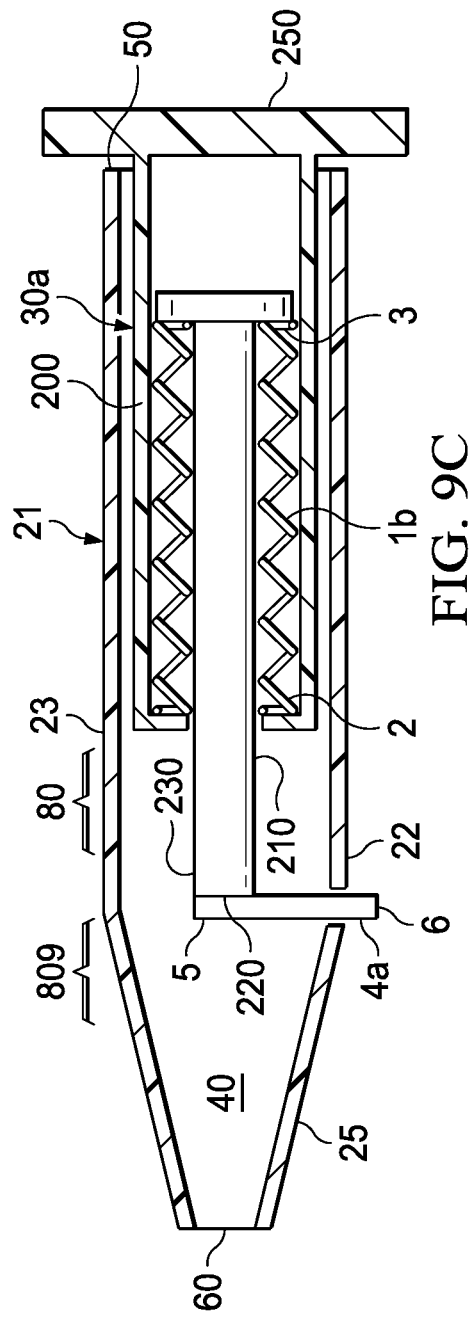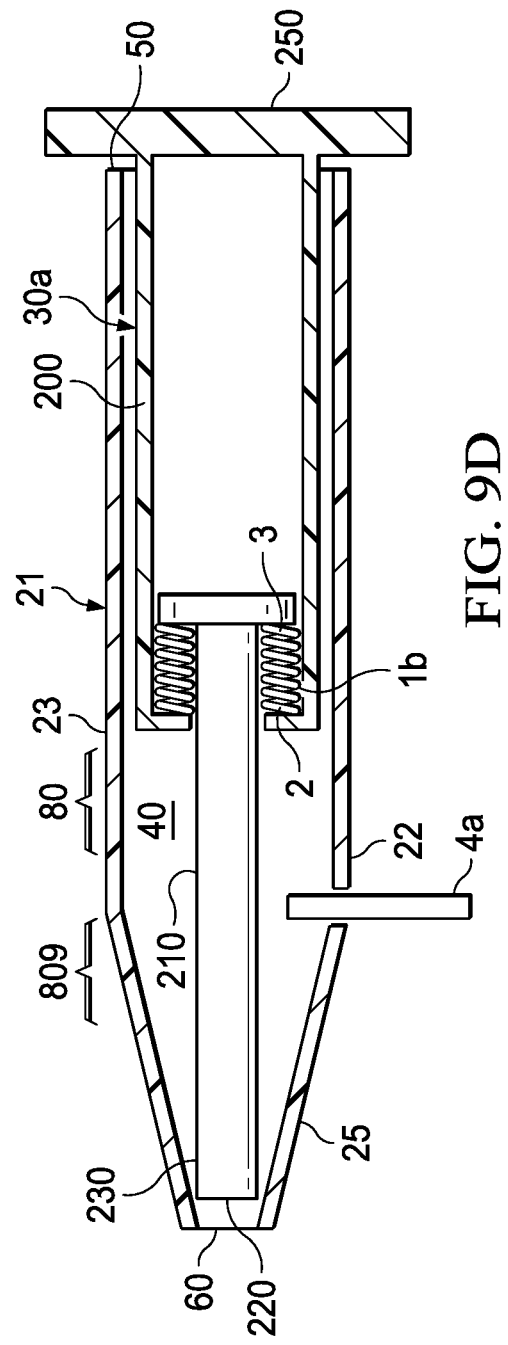

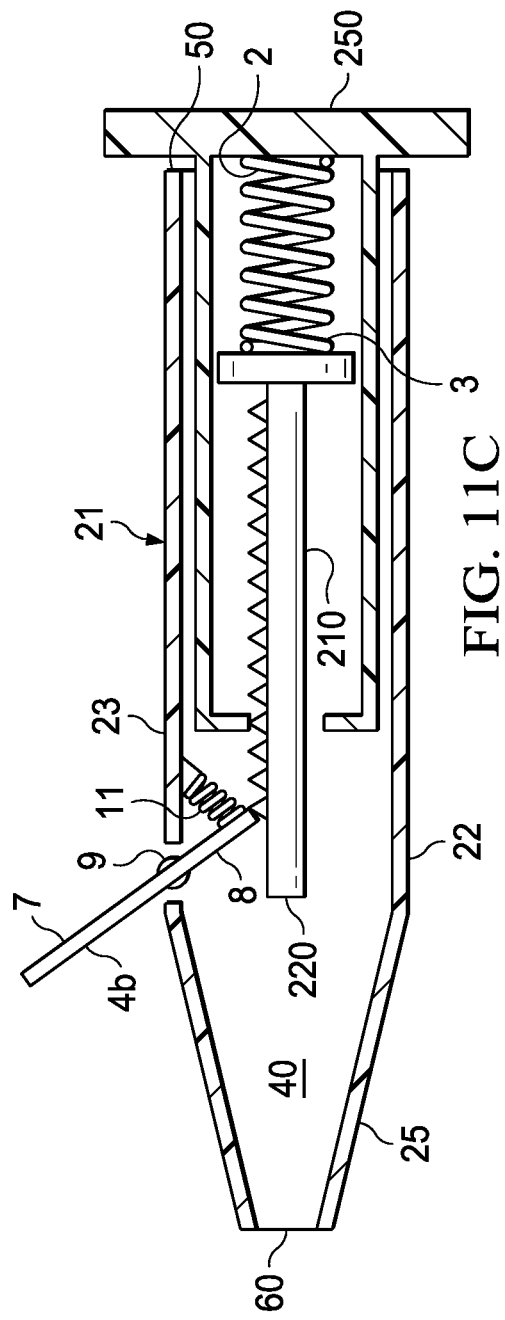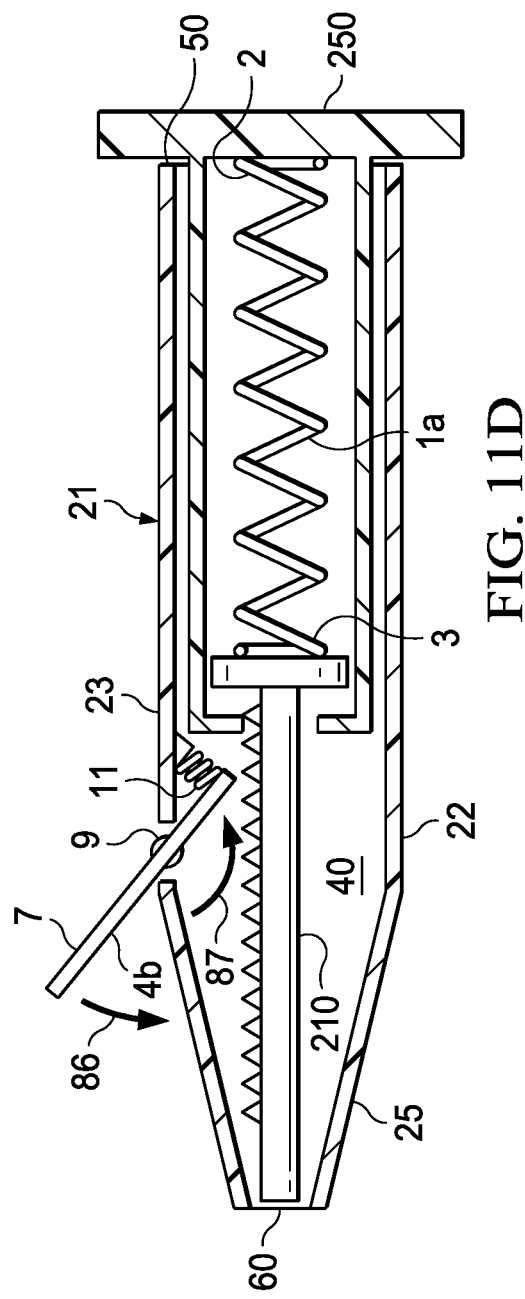

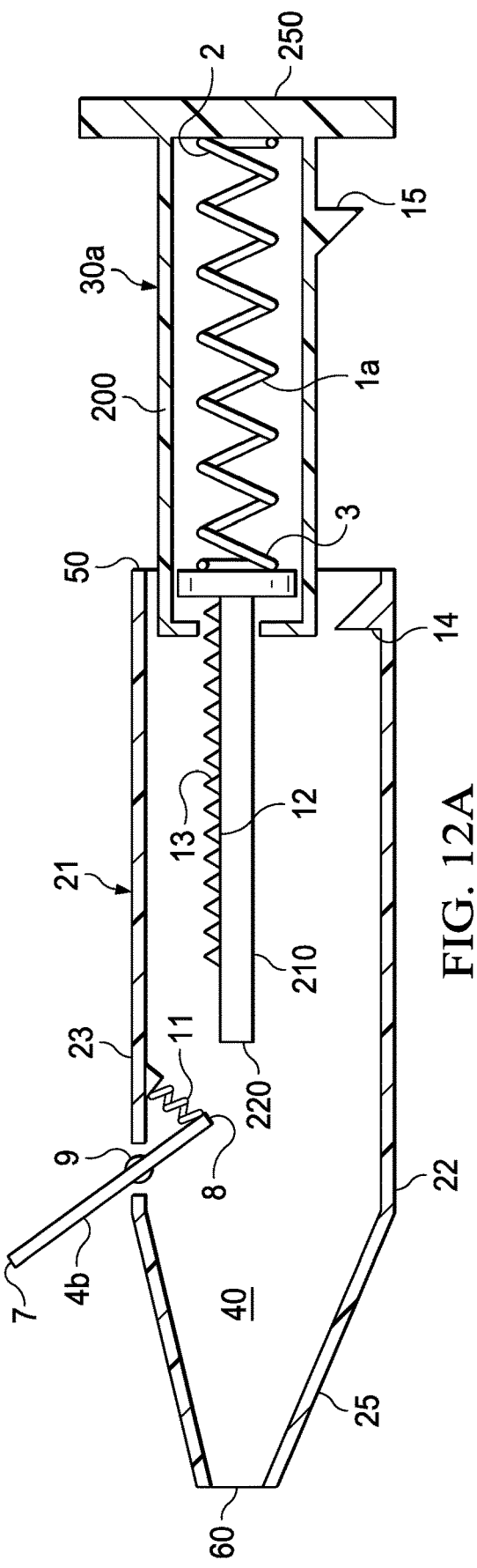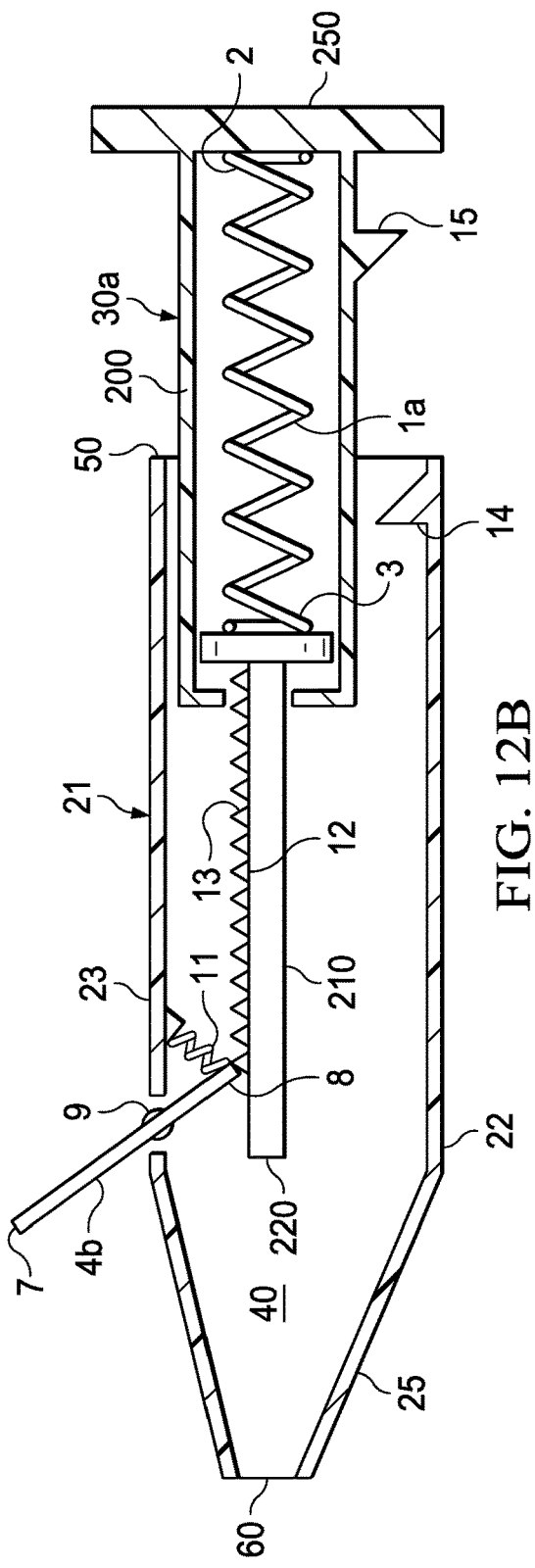

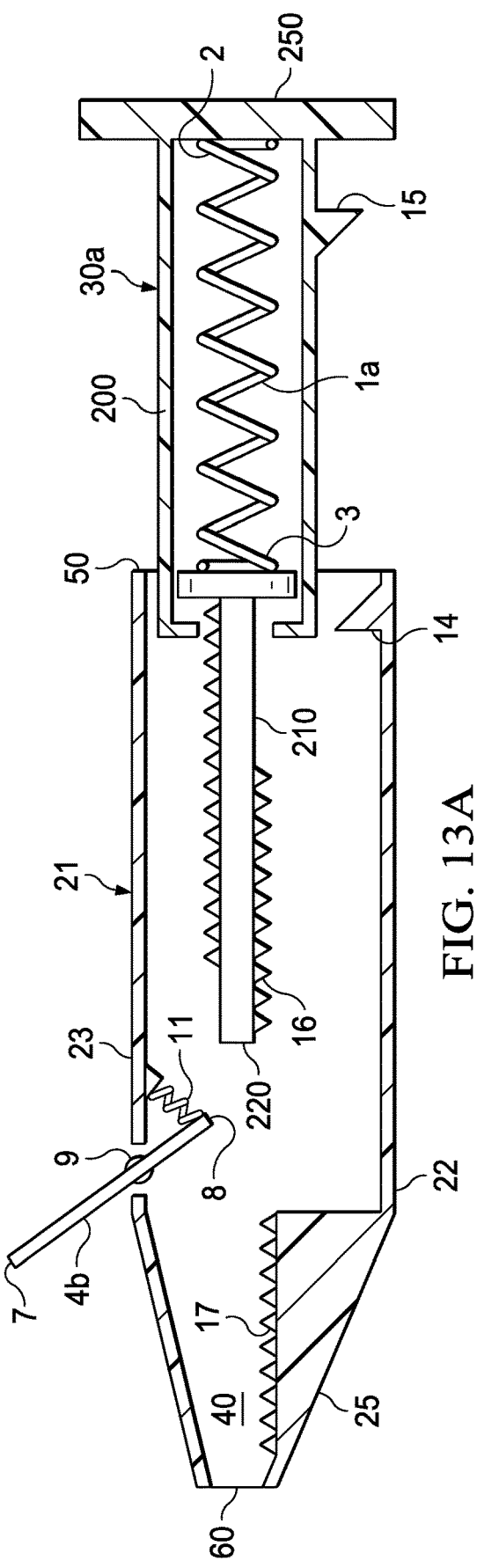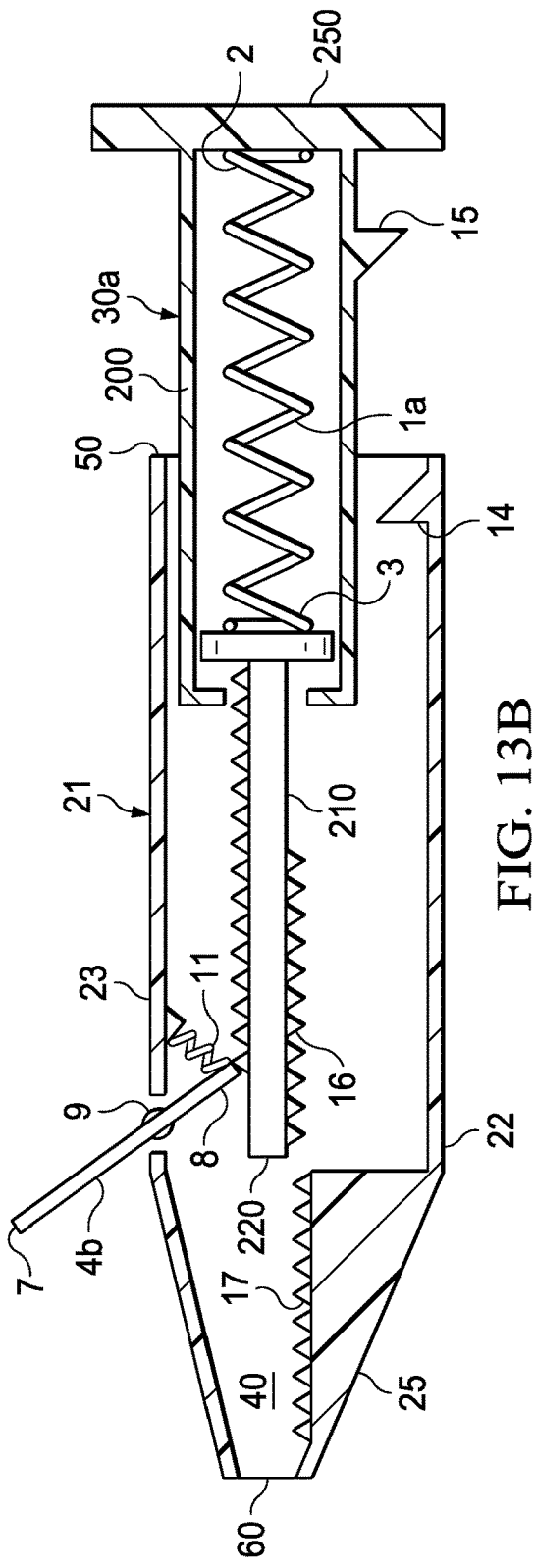
FIG. 13A
FIG. 13B

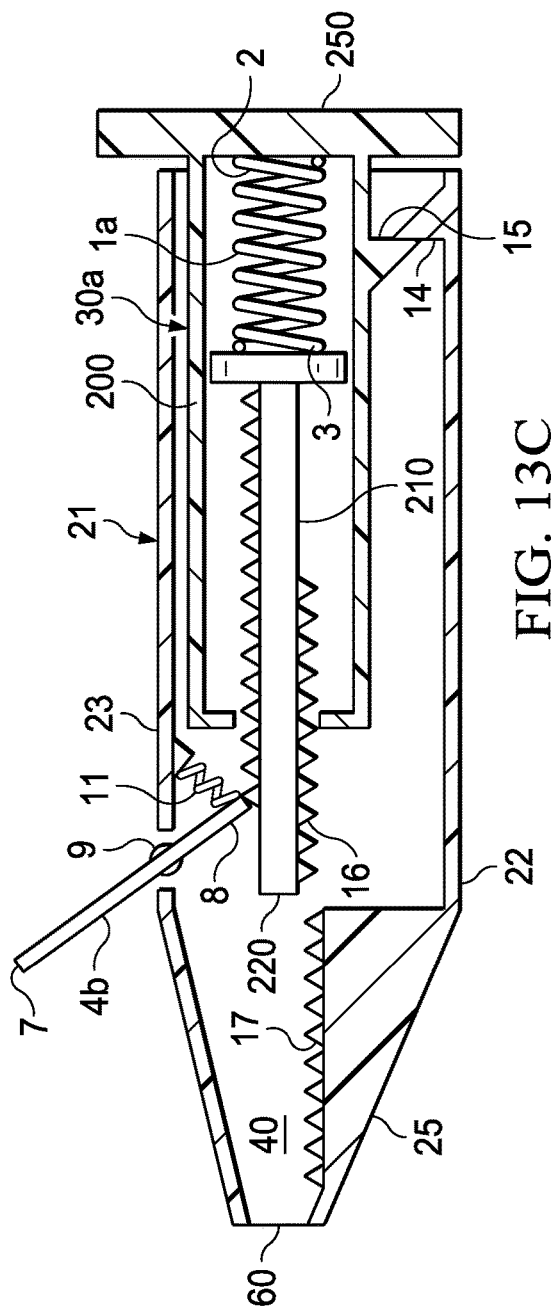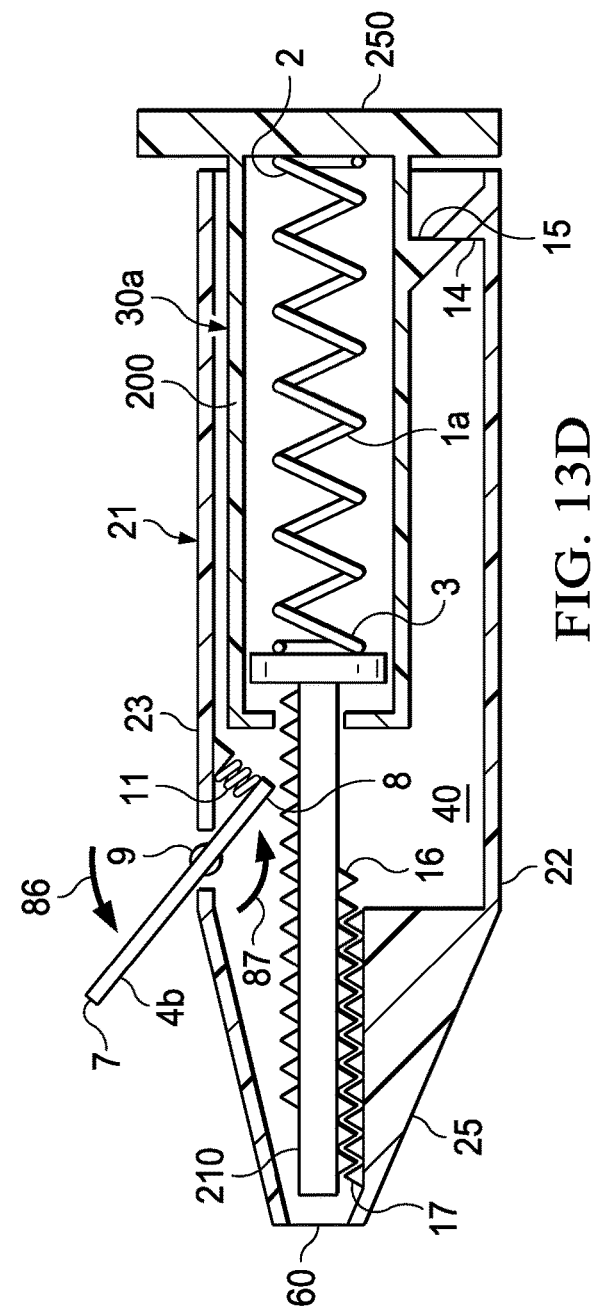

IOL INJECTOR HAVING A SPRING-ASSISTED IOL DELIVERY MECHANISM

CROSS-REFERENCE TO RELATED APPLICATIONS

This application claims priority to U.S. Provisional Application Ser. No. 62/781,719, filed on Dec. 19, 2018, the contents of which is incorporated herein by reference in its entirety.

TECHNICAL FIELD

The present disclosure relates to systems, apparatuses, and methods for intraocular lens (IOL) injectors.

BACKGROUND

The human eye in its simplest terms functions to provide vision by transmitting and refracting light through a clear outer portion called the cornea, and further focusing the image by way of the lens onto the retina at the back of the eye. The quality of the focused image depends on many factors including the size, shape, and length of the eye, and the shape and transparency of the cornea and lens. When trauma, age, or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial lens (IOL).

Many cataractous lenses are removed by a surgical technique called phacoemulsification. During this procedure, an opening is made in the anterior capsule of an eye and a phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced with an IOL.

The IOL may be injected into the eye through a small incision, sometimes the same incision used to remove the diseased lens. An IOL injector may be used to deliver an IOL into the eye.

SUMMARY

An intraocular lens (IOL) injector is described. The IOL injector includes an injector body having a main body having a proximal end and a distal end, a nozzle having a proximal end and a distal end, the proximal end of the nozzle coupled to the distal end of the main body, and a bore having a longitudinal axis extending from the proximal end of the main body to the distal end of the nozzle. The IOL injector also has a spring-assisted plunger movably coupled within the injector body and aligned within the bore. The plunger has a plunger body having a proximal end accessible to a user and a distal end, a plunger rod having a proximal end and a distal end, a plunger tip formed at the distal end of the plunger rod and adapted to contact an IOL and axially move the IOL in response to an axial force applied to the plunger; and a spring having a first end coupled to the plunger body and a second end coupled to the plunger rod. In response to an axial force applied to the plunger body, the plunger body is adapted to move axially, and in response, the spring is adapted to store elastic energy. In response to release of stored elastic energy from the spring, the plunger rod is adapted to move axially toward the distal end of the injector body.

The nozzle may include an IOL storage location configured to house an IOL, and an IOL dwell location distal to the IOL storage location. In response to a first axial force applied to the plunger body, the plunger body may be adapted to move axially from a proximal position to a first distal position. In response, the plunger rod may be adapted to move axially from a first position proximally adjacent to the IOL storage location to a second position proximally adjacent to the IOL dwell position, and contact a removable stop coupled to the injector body and adapted to prevent further axial movement of the plunger rod. In response to a further axial force applied to the plunger body, the plunger body may be adapted to move axially from the first distal position to a second distal position, and in response, the spring may be adapted to store elastic energy. In response to removal of the removable stop, the plunger rod may be adapted to move axially toward the distal end of the injector body in response to the release of stored elastic energy from the spring.

The removable stop may include a pin slidably disposed within a first side of the injector body. A first end of the pin may be accessible to a user; and a second end of the pin may be adapted to contact the plunger rod. In a first configuration, the second end of the pin may be adapted to contact the plunger rod and configured to prevent axial movement of the plunger rod. In a second configuration, the second end of the pin may be adapted not to prevent axial movement of the plunger rod.

The removable stop may include a braking mechanism adapted to provide resistance to axial movement of the plunger rod. The braking mechanism may include a brake lever having a first end having a handle accessible to a user and a second end adapted to contact the plunger rod and thereby apply a frictional braking force against axial movement of the plunger rod. The brake lever may be coupled to the injector body at a pivot point disposed between the first and second ends of the brake lever. The braking mechanism may include a brake lever return spring having a first end coupled to the brake lever and a second end coupled to the injector body. In response to a force applied to the handle, the second end of the brake lever may be adapted to move away from a resting position in contact with the plunger rod, thereby decreasing the frictional braking force. In response to the decreased frictional braking force, the plunger rod may be adapted to axially move in response to release of stored elastic energy from the spring. The brake lever return spring may be adapted to return the second end of the brake lever to the resting position.

The plunger rod may include a brake pad having one or more brake pad ribs adapted to contact the second end of the brake lever, and thereby apply a frictional braking force against axial movement of the plunger rod.

The frictional braking force may have a value B, the force applied to the handle may have a value H, and B may be inversely related to H.

The spring may be a compression spring, a tension spring, or a torsion spring.

The plunger may have a telescoping portion wherein a proximal portion of the plunger rod is concentrically coupled within a distal portion of the plunger body and axially slidable therein. In response to an axial force applied to the plunger body, the proximal portion of the plunger rod may be adapted to slidably move within the distal portion of the plunger body, and in response to release of stored elastic energy from the spring, the proximal portion of the plunger rod may be adapted to slidably move within the distal portion of the plunger body.

The injector body may include at least one ridge disposed within the bore, and the plunger body may include at least one ridge-engaging tooth. The at least one ridge and the at least one ridge-engaging tooth may be adapted to prevent movement of the plunger body away from the distal end of the injector body of the IOL injector.

The ridge and the ridge-engaging tooth may be adapted to prevent movement of the plunger body away from the distal end of the injector body of the IOL injector when the plunger body is in the second distal position.

The IOL injector may include a ribbed damping mechanism configured to provide frictional resistance to axial movement of the plunger rod. The ribbed damping mechanism may include at least one damping rib disposed on the plunger rod and at least one damping rib disposed within the bore. The at least one damping rib on the plunger rod may be configured to contact the at least one damping rib disposed within the bore and adapted to provide a frictional resistance to axial movement of the plunger rod.

The ribbed damping mechanism may be configured to apply an increasing frictional resistance to axial movement of the plunger rod as a function of decreasing distance of the plunger rod from the distal end of the nozzle.

The at least one damping rib on the plunger rod and/or the at least one damping rib disposed within the bore may include a plurality of damping ribs, and a distance between each of the damping ribs may decrease with decreasing distance from the distal end of the nozzle.

The at least one damping rib on the plunger rod and/or the at least one damping rib disposed within the bore may include a plurality of damping ribs, and a number of damping ribs on the plunger rod contacting a number of damping ribs disposed within the bore may increase with decreasing distance from the distal end of the nozzle.

The IOL injector may have an IOL injection force profile defining a relationship between an axial location of an IOL within the bore (AP) and a force applied by a user to axially move an IOL within the bore (AF). The IOL injector may be configured to have a force profile having minimal variability of AF as a function of AP.

The IOL injector may be adapted to separately inject an IOL base, an IOL optic, or both.

The IOL injector may be adapted to concurrently inject an IOL base and an IOL optic.

BRIEF DESCRIPTION OF THE DRAWINGS

For a more complete understanding of the present disclosure, reference is now made to the following description, taken in conjunction with the accompanying drawings, which are not to scale, and in which:

FIG. 8A is a schematic of an example IOL injector having a compression spring assisted plunger;

FIG. 8B is another schematic of the example IOL injector of FIG. 8A;

FIG. 8C is yet another schematic of the example IOL injector of FIG. 8A;

FIG. 8D is still another schematic of the example IOL injector of FIG. 8A;

FIG. 9A is a schematic of an example IOL injector having a tension spring assisted plunger;

FIG. 9B is another schematic of the example IOL injector of FIG. 9A;

FIG. 9C is yet another schematic of the example IOL injector of FIG. 9A;

FIG. 9D is still another schematic of the example IOL injector of FIG. 9A;

FIG. 11C is yet another schematic of the example IOL injector of FIG. 11A;

FIG. 11D is still another schematic of the example IOL injector of FIG. 11A;

FIG. 12A is a schematic of an example IOL injector having a ridge and a ridge-engaging tooth adapted to prevent movement of the plunger body away from the distal end of the injector body;

FIG. 12B is another schematic of the example IOL injector of FIG. 12A;

FIG. 13A is a schematic of an example IOL injector having a plunger advancement damping mechanism;

FIG. 13B is another schematic of the example IOL injector of FIG. 13A;

FIG. 13C is yet another schematic of the example IOL injector of FIG. 13A;

FIG. 13D is still another schematic of the example IOL injector of FIG. 13A;

DETAILED DESCRIPTION

Figure 1:
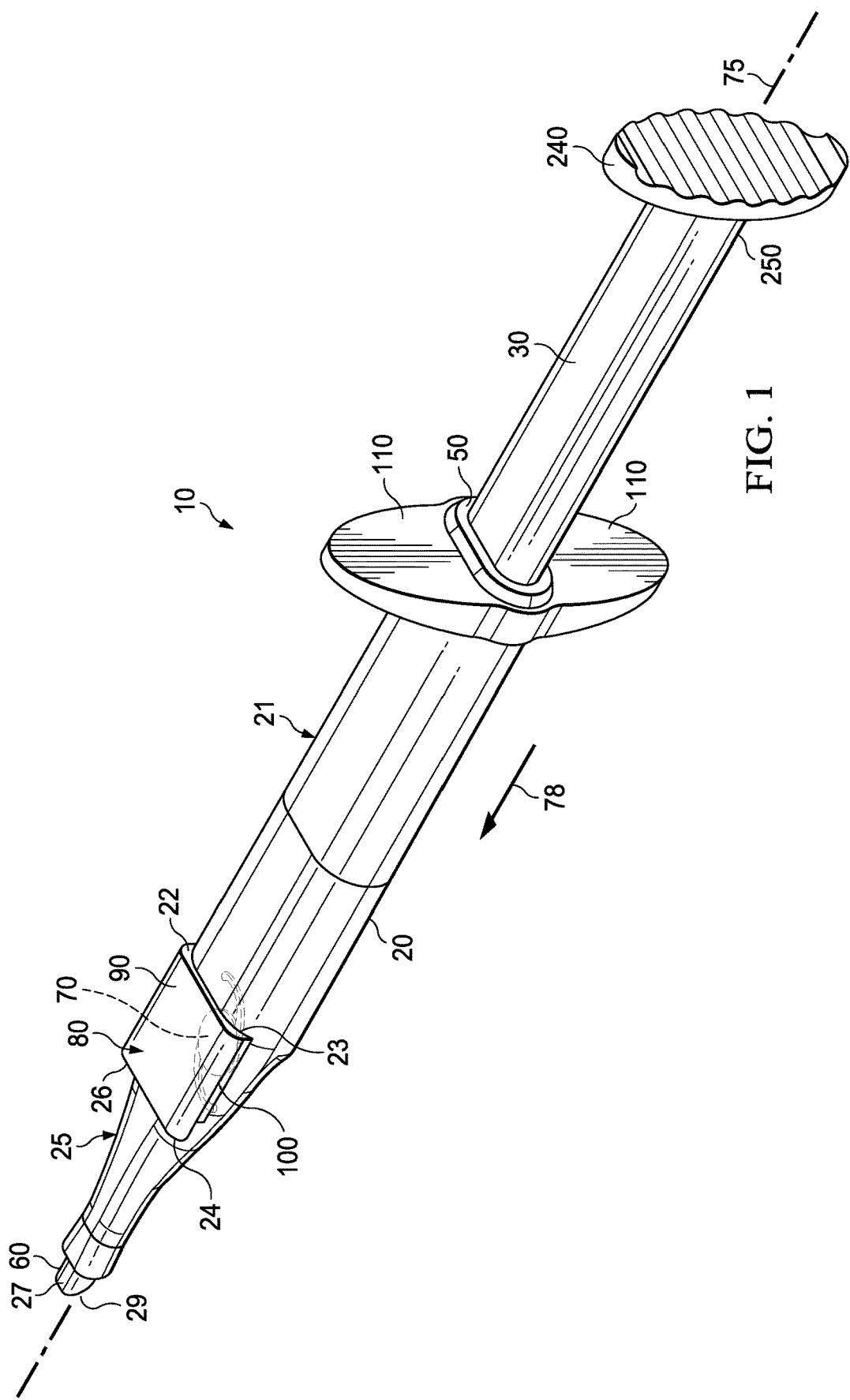
FIG. 1 is a perspective view of an example IOL injector.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Figure 2:
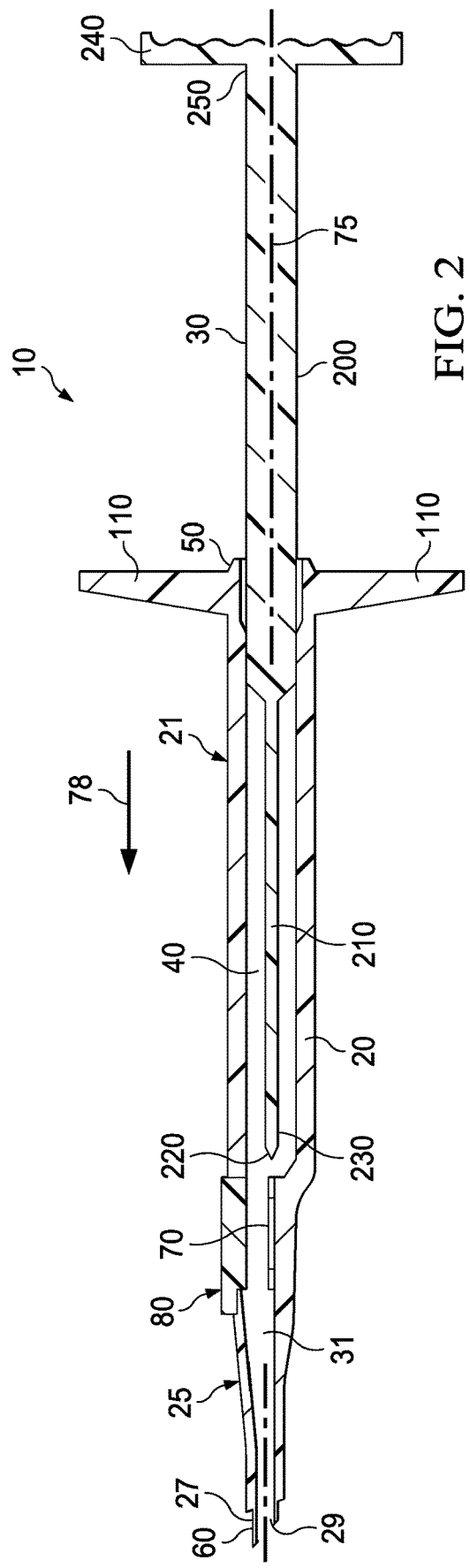
FIG. 2 is a longitudinal cross-sectional view of the example IOL injector of FIG. 1.

FIGS. 1 and 2 are schematics of an example IOL injector 10 that is actuated by manual user application of force. The IOL injector 10 includes an injector body 20, a plunger 30 adapted to reciprocate through a bore 40 formed in the injector body 20. The injector body 20 has a main body 21 having a proximal end 50 and a distal end 23, and a nozzle 25 having a proximal end 22 and a distal end 60. The proximal end 22 of the nozzle 25 is coupled to the distal end 23 of the main body 21. The nozzle 25 has an IOL storage location 80 configured to house an uncompressed IOL 70, and an IOL dwell location 809 distal to the IOL storage location 80.

The bore 40 extends from the proximal end 50 of the main body 21 to the distal end 60 of the nozzle 25. A distal portion of the bore 40 within the nozzle 25 forms a tapered delivery channel 31 through which an IOL may be axially advanced, compressed, and delivered into an eye via an opening 29 in distal tip 27 at distal end 60.

The plunger 30 is movably coupled within the injector body 20 and aligned within the bore 40. The plunger 30 has a plunger tip 220 adapted to contact an IOL 70.

The IOL injector 10 also includes a longitudinal axis 75. The longitudinal axis 75 may extend along the plunger 30 and define a longitudinal axis of the plunger 30.

The IOL storage location 80 may include a door 90 to provide access to the interior of the IOL storage location 80. The door 90 may include a hinge 100 such that the door 90 may be pivoted about the hinge 100 to open the IOL storage location 80 and, for example, allow the installation of the IOL 70. In other implementations, the IOL storage location 80 may exclude a door for installing the IOL 70. In such instances, the IOL 70 may be incorporated into the IOL storage location 80 at the time of assembly of the IOL injector 10. Thus, in such instances, the IOL injector 10 would be a preloaded IOL injector. In such instances, the IOL storage location 80 may have a cover that is not configured to open, rather than a door 90. The IOL storage location 80 may include a hole adapted to allow addition of viscoelastic into the IOL storage location 80.

The injector body 20 may also include tabs 110 formed at the proximal end 50 of the injector body 20. The tabs 110 may be manipulated by fingers, thumb, or hand of a user, such as an ophthalmologist, an ophthalmic surgical assistant or nurse, or other medical professional, to advance the plunger 30 through the bore 40.

The plunger 30 may include a plunger body 200, a plunger rod 210 extending distally from the plunger body 200, and a plunger tip 220 formed at the distal end 230 of the plunger rod 210 and adapted to contact an IOL disposed, for example, with the IOL storage location 80 of the IOL injector 10. As the plunger 30 is axially advanced and thereby displaced distally within the bore 40 in the direction of the arrow 78, the plunger tip 220 of the plunger 30 is adapted to engage and advance the IOL, such as IOL 70. In FIGS. 1 and 2, the IOL 70 is shown located within the IOL storage location 80. The plunger 30 may also include flanges 240 formed at proximal end 250, which may be manipulated by the fingers, thumb, or hand of a user to advance the plunger 30 through the bore 40 by displacing the plunger 30 through the bore 40 distally in the direction of the arrow 78.

Figure 3A:
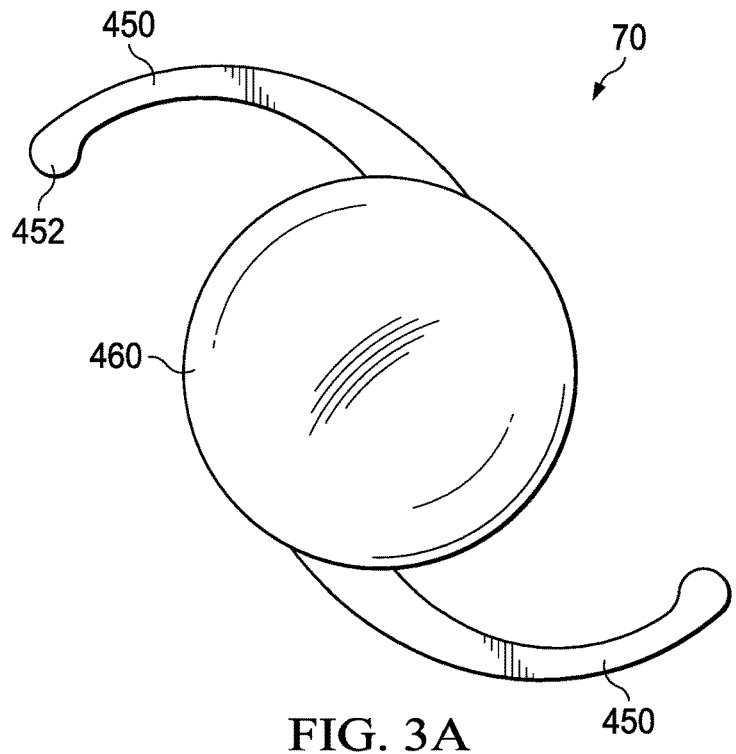
FIG. 3A shows an example one-piece IOL.

In some implementations, the IOL 70 may be a one-piece IOL. That is, in some implementations, the IOL 70 may include an optic 460 and haptics 450, as shown in FIG. 3A. Each of the haptics 450 include a tip 452. In some implementations, the optic 460 and the haptics 450 may be integrally formed out of a single piece of material. In other implementations, the optic 460 may be formed out of one piece of material; the haptics 450 may be formed out of another piece of material, and the optic 460; and the haptics 450 may be coupled together prior to delivery into an eye. In some instances, the optic 460 and haptics 450 may be fixedly secured to each other prior to insertion into an IOL injector and delivered into an eye.

Figure 3B:
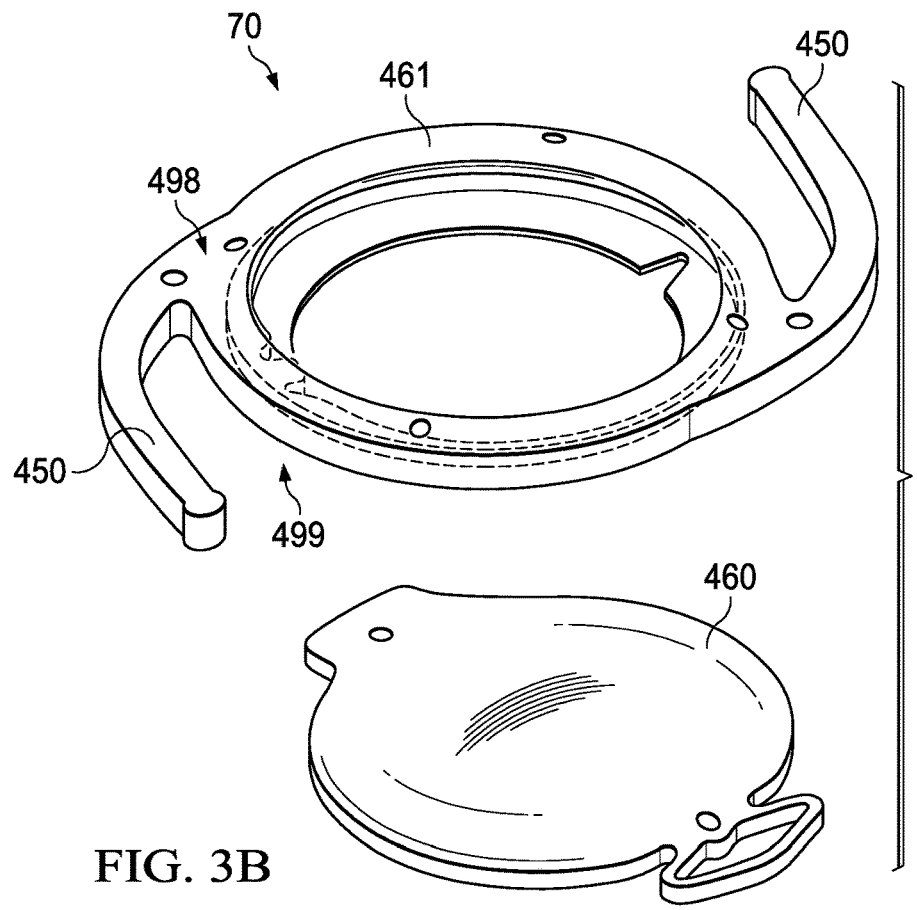
FIG. 3B shows an example two-piece IOL including a base and an optic.
Figure 4:
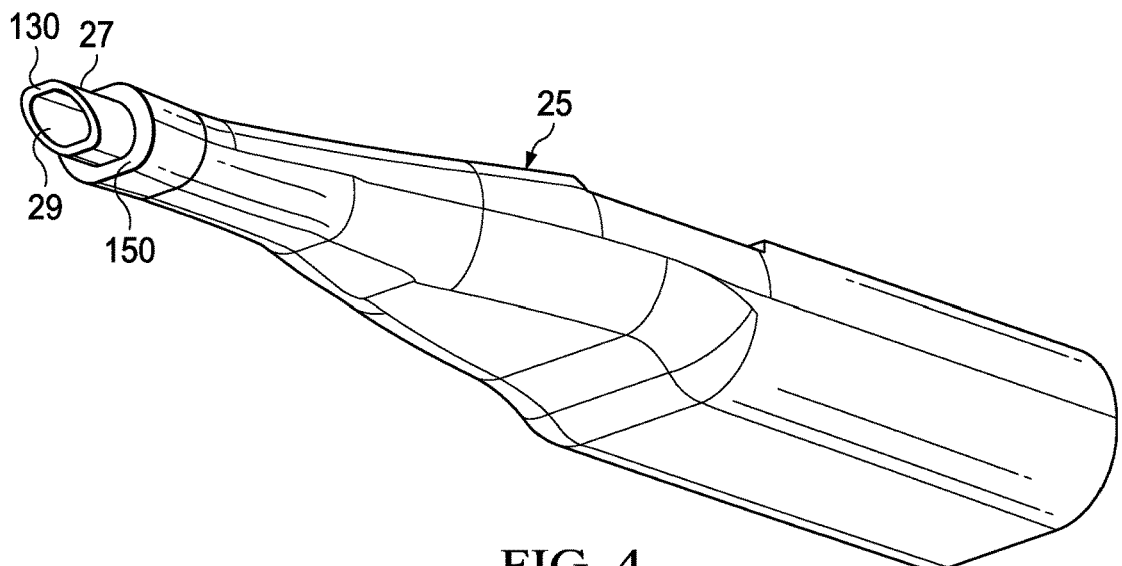
FIG. 4 is a perspective view of an example nozzle of an IOL injector.
Figure 5A:
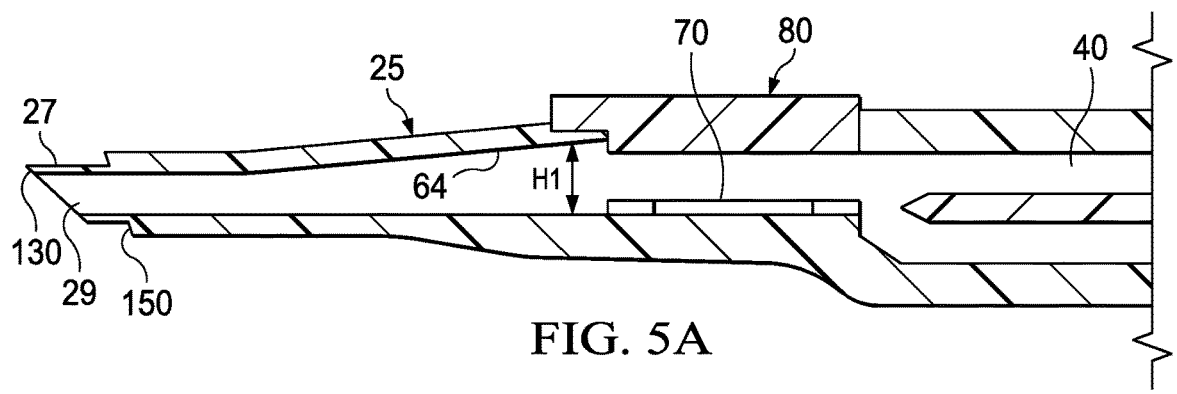
FIG. 5A is a cross-sectional view of the nozzle of the IOL injector of FIG. 4.
Figure 5B:
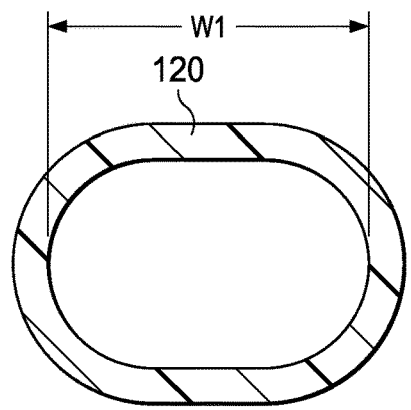
FIG. 5B is another cross-sectional view of the nozzle of the IOL injector of FIG. 4.

In other implementations, the IOL 70 may be a multi-piece IOL, as shown, for example, in FIG. 3B. For example, in some implementations, the IOL 70 be include two or more separate components. FIG. 3B is an example IOL 70 that includes two removably attached components. As shown in FIG. 3B, the IOL 70 includes an optic 460 and a base 461 that includes haptics 450 and that has a top 498 and a bottom 499. The optic 460 and the base 461 are adapted to be coupled together into a unitary IOL and, thereafter, detached from each other into separate components, if desired. In some instances, one or more components of a multi-piece IOL, such as, for example the two-piece IOL 70 shown in FIG. 3B, are separately injectable into a patient's eye. Once in the eye, the components may be assembled into a complete IOL. For example, in the case of the two-piece IOL 70 shown in FIG. 3B, the optic 460 and the base 461 are separately injectable into an eye. Once injected, the optic 460 is adapted to be coupled to the base 461 within the groove 14 disposed within an inner edge 8 of the base 461.

Occasionally, patients may require replacement of an IOL, and a procedure to replace an IOL may result in damage to the eye. With the use of a two-piece IOL, for example, a replacement procedure may involve replacement only of the optic, allowing the base to remain in place within the eye.

As explained above, in some implementations, the IOL 70 may be a two-piece IOL wherein the base 461 and the optic 460 are separately injected into the patient's eye. Accordingly, for two-piece IOLs, the base 461 and the optic 460 may be contained in separate IOL injectors 10 for insertion in the eye. In other implementations, the two components of a two-piece IOL may be inserted into an eye separately using a single IOL injector. For a single piece IOL, the optic 460 and haptics 450 form a unitary IOL and are inserted into an eye simultaneously with the use of a single IOL injector.

Accordingly, in some implementations, a user may place a one-piece IOL into an IOL injector, for example, by loading an IOL into an IOL storage compartment of the IOL injector, such as the IOL storage location 80 of the IOL injector described above. As also explained, the IOL storage location 80 may be accessed via a door, such as the door 90.

In the case of a two-piece IOL, in some implementations, a user may load the base, such as base 461, into an IOL storage compartment of an IOL injector, for example, via a door. The optic such as optic 460, may be introduced into the IOL storage compartment of a separate IOL injector, for example, via a door. In some instances, the IOL storage compartment may be accessed through the door such as door 90.

In some implementations, the IOL may be pre-loaded into the storage compartment of an IOL injector, for example, during manufacturing or otherwise prior to distribution to an end user. Accordingly, for the one-piece IOL, the one-piece IOL may be pre-loaded into the storage compartment an IOL injector prior to receipt by the end user. For a two-piece IOL, the base may be pre-loaded into a storage compartment of one IOL injector, while the optic may be pre-loaded into the IOL storage compartment of another IOL injector. The term "pre-loaded" as used herein means that an IOL, either in a one-piece or multi-piece configuration (including, for example, a two-piece configuration) is loaded into the IOL injector not by a user, but, rather, the IOL is installed in the IOL injector before and is already contained within the IOL injector when the IOL injector is received by the user. The IOL injector(s) may be packaged within sterile packaging when received by a user.

As would be understood by persons of ordinary skill in the art upon reading the present disclosure, an IOL that is pre-loaded into an IOL injector has advantages over manual installation and folding of an IOL into the IOL injector that is performed by a user. For example, manual installation and folding of an IOL may allow more opportunity for errors, which have the potential to cause unnecessary secondary manipulation or correction during an already complex procedure. For example, manual installation and folding of an IOL may also introduce the possibility of contamination of the IOL, such as by human error or poor sterile technique. Contamination of the IOL may compromise the sterile environment for the patient and risk infection or other harm to the patient.

FIGS. 4-7 illustrate details of the example nozzle 25. In some instances, the nozzle 25 has a tapered exterior surface. Further, the nozzle 25 may include a portion of the bore 40 forming a tapered delivery channel 31 that tapers towards the opening 29. The distal tip 27 is adapted for insertion into an eye so that the IOL 70 may be implanted. The IOL 70 is expelled from the opening 29 formed in the distal tip 27 into the eye. As shown in FIG. 5B, tapered delivery channel 31 and the distal tip 27 may have an elliptical cross section 120 having a width W1. Additionally, the distal tip 27 may include a beveled tip 130. The IOL storage location 80, delivery channel 31, and opening 29 may define a delivery passage. A size of the delivery passage may vary along its length. For example, in some instances, the width W1, a height H1, or both, of the delivery passage may change along a length of the delivery passage. The variation in size of the delivery passage may contribute to the compression of the IOL as it is advanced therealong through the delivery passage.

In some instances, the injector body 20 may include an insertion depth guard 140. The insertion depth guard 140 may form a flanged surface 150 that is adapted to abut an exterior eye surface. The insertion depth guard 140 abuts an eye surface and, thereby, limits an amount by which the distal tip 27 is permitted to extend into an eye, as described in U.S. application Ser. No. 15/049,315, the disclosure of which is being incorporated herein by reference in its entirety.

Figure 6:
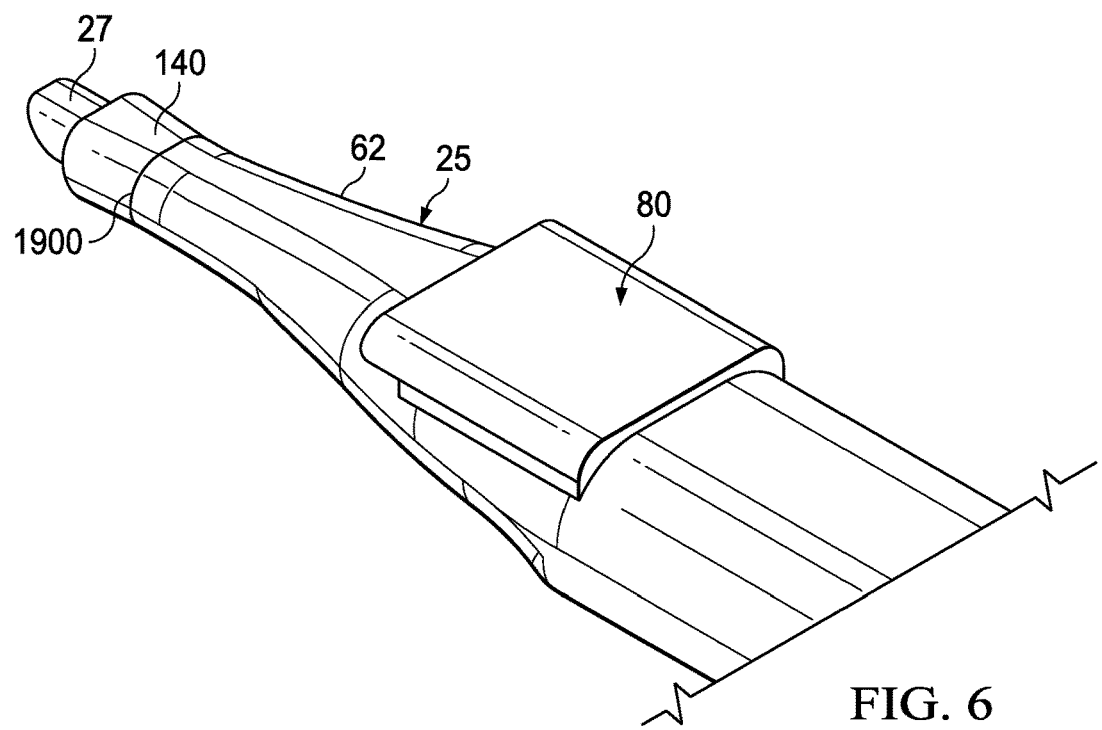
FIG. 6 is another perspective view of the nozzle of the IOL injector of FIG. 4.
Figure 7:
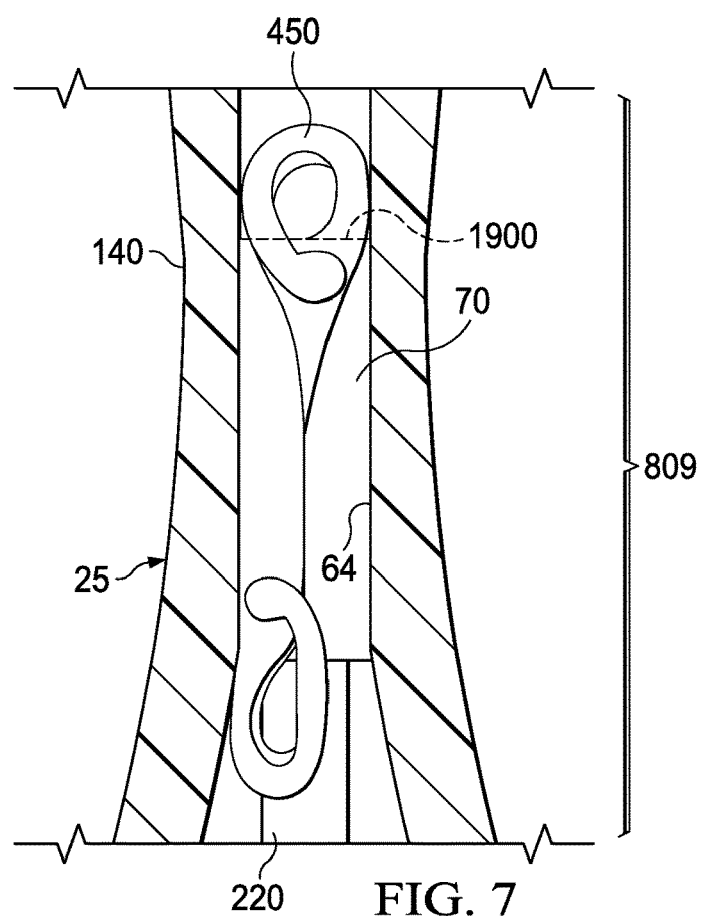
FIG. 7 is a view of a distal end of an example IOL injector with an IOL located therein and positioned in a dwell location.
Figure 10A:
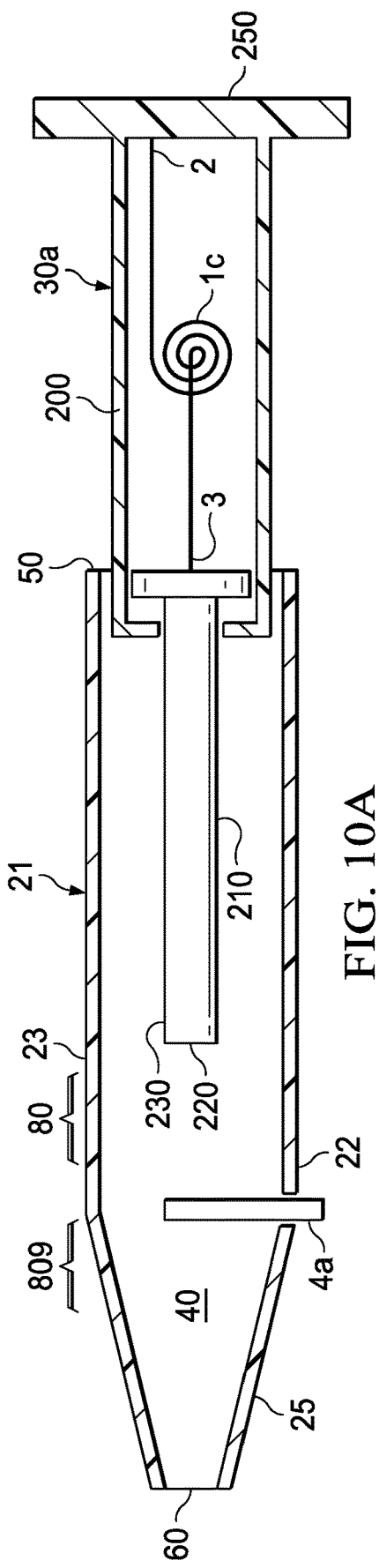
FIG. 10A is a schematic of an example IOL injector having a torsion spring assisted plunger.
Figure 10B:
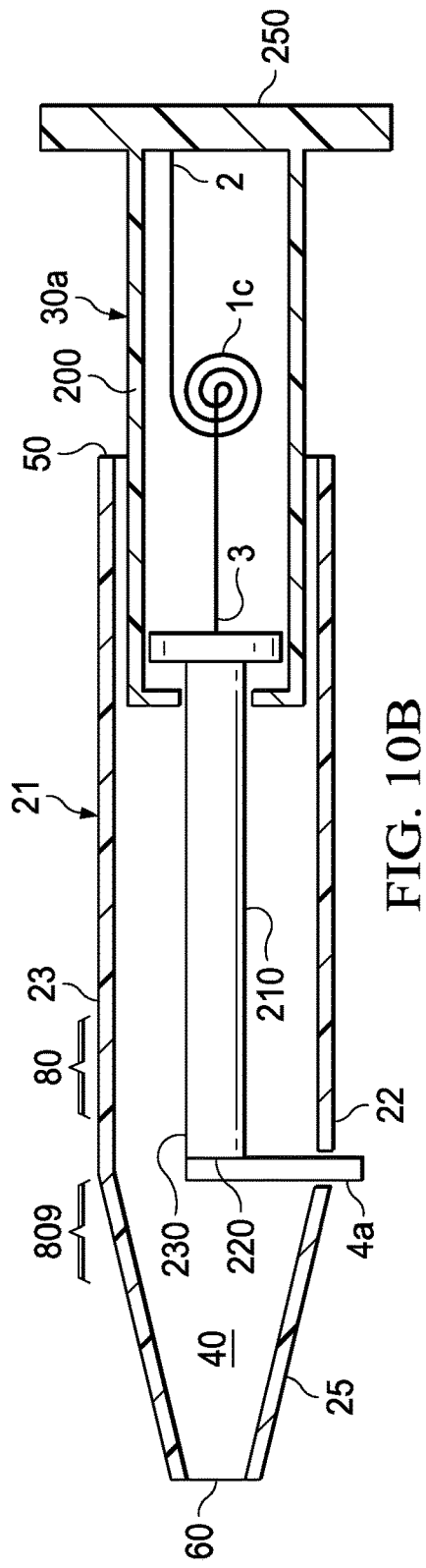
FIG. 10B is another schematic of the example IOL injector of FIG. 10A.
Figure 10C:
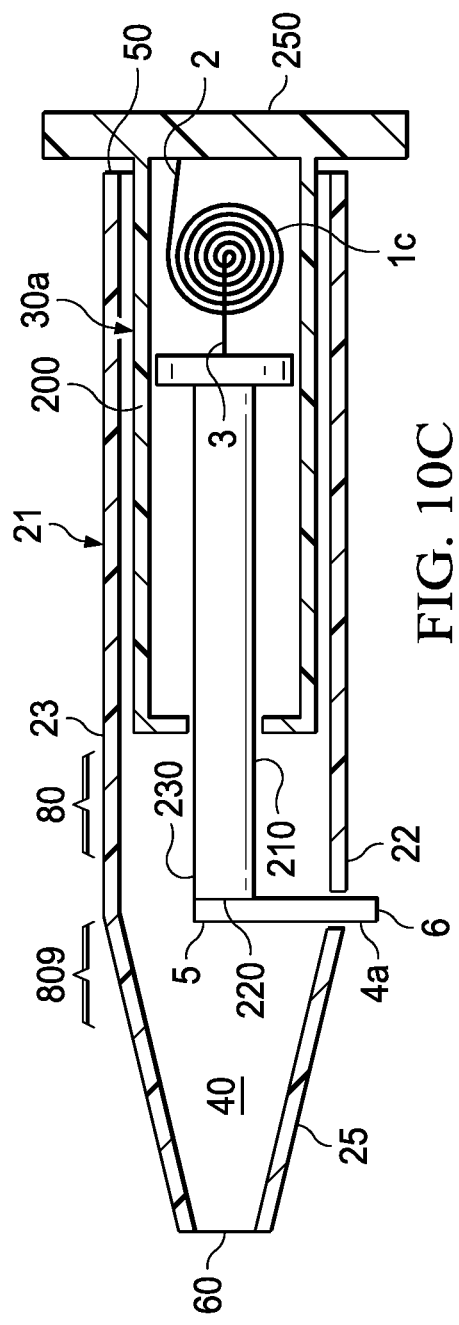
FIG. 10C is yet another schematic of the example IOL injector of FIG. 10A.
Figure 10D:
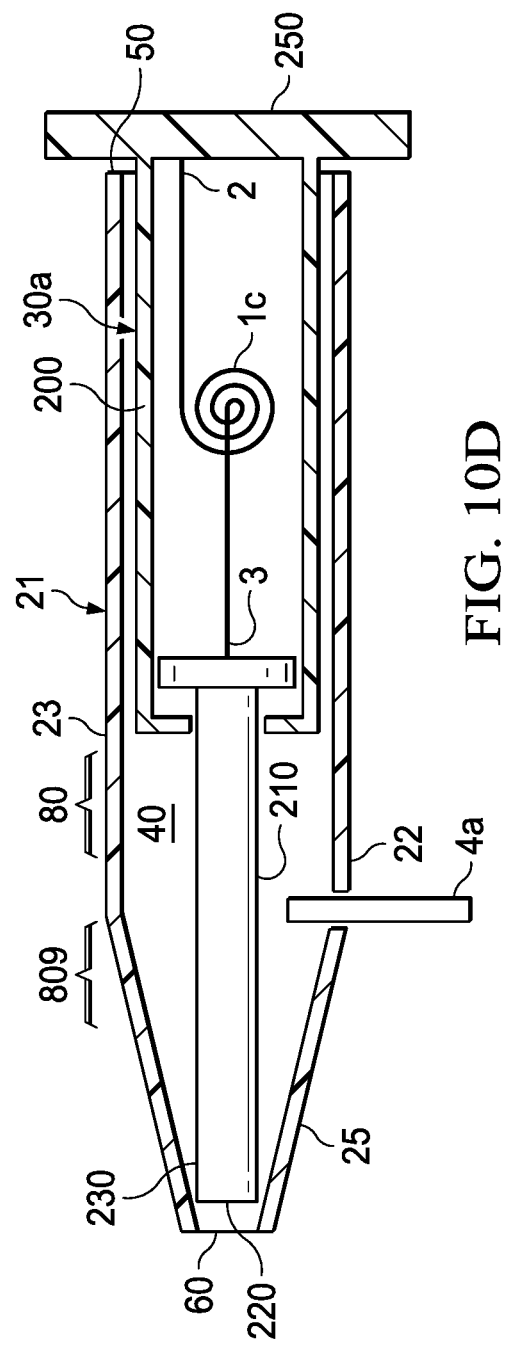
FIG. 10D is still another schematic of the example IOL injector of FIG. 10A.

FIG. 6 and FIG. 7 are detail views of a portion of the example nozzle 25. The nozzle 25 may include a tapered portion 62 and the insertion depth guard 140. The distal tip 27 may include a demarcation 1900 that provides a visual indication or a dwell location 809 of a compressed or partially compressed IOL 70. The term "dwell location" as used herein refers to a location adjacent to the distal end 60 of the nozzle 25. For example, the dwell location 809 may be a location 2-10 mm from the distal end 60. For example, in the example shown in FIG. 6, the demarcation 1900 is a narrow ridge or line that encircles all or a portion of the nozzle 25. In some instances, the demarcation 1900 may be disposed between the tapered portion 62 and the insertion depth guard 140. At least a portion of the injector body 20 may be formed from a transparent or semi-transparent material that permits a user to see an IOL within the injector body 20. Particularly, the nozzle 25 of the injector body 20 may be formed from a transparent material to permit observation of the IOL as it is moved therethrough by the plunger 30.

FIG. 7 shows a view of the distal end 60 of the IOL injector 10 with an IOL 70 located therein at a dwell position 809 in nozzle 25. As shown in FIG. 7, the dwell position 809 of the IOL 70 may be defined as a location where a distal edge of the optic of the IOL 70 substantially aligns with the demarcation 1900. A haptic 450 or a portion thereof may extend beyond the demarcation 1900.

Due to the sensitivity and delicacy of ocular tissues and structures, it is important that the user is able to deliver the IOL to a patient's eye with acceptable peak speed and applied actuation force.

Typically, the mechanism of compressing and advancing the IOL by existing IOL injectors involves substantial variation in force required to advance the plunger through the IOL injector. For example, during actuation of existing IOL injectors, there is typically a peak resistance to IOL advancement when the IOL is fully compressed within the nozzle, which is followed by a pressure release when the IOL is at the exit of the nozzle. In some cases, this can cause the IOL to be ejected with high velocity in a less controllable manner. The IOL advancement resistance force peaks and troughs associated with some existing IOL injectors can reduce user control of the IOL injector and the IOL delivery. The challenges of delivering the IOL include, for example, ensuring that the mechanism and magnitude of force applied through user actuation of the IOL injector is appropriate and repeatable. It is also preferable to have an IOL injector that is intuitive to use and can be utilized by users of the entire spectrum of skills and techniques.

In various implementations described herein, the present disclosure relates to a spring-assisted plunger mechanism adapted to solve the problems described above. Advantages of the spring-assisted plunger mechanism described herein include, without limitation providing a consistent actuation force experience for the user, preventing sudden IOL ejection, providing higher reliability and comfort for the user, with improved safety.

In general, the spring-assisted plunger mechanism described herein is adapted such that initial user actuation of the spring assisted plunger mechanism results in storage of elastic energy. Subsequently, the spring assisted plunger mechanism is adapted to release the stored elastic energy, which assists in advancing the plunger to deliver the IOL to an eye of a patient. Furthermore, in some implementations, the spring assisted plunger mechanism described herein includes a damping mechanism adapted to provide resistance against sudden ejection of the IOL from the IOL injector.

FIGS. 8A-13D are schematics of IOL injectors having various example implementations of the spring-assisted plunger mechanism of the present disclosure.

In some implementations, the spring-assisted plunger mechanism includes one or more springs configured to provide a mechanical force to drive or assist axial advancement of the plunger rod 210 toward the distal end 60 of the nozzle 25.

The term "spring" as used herein refers to an elastic object that is adapted to store mechanical energy. More specifically, without limitation to theory, a spring is a device that stores potential energy, specifically elastic potential energy, by straining the bonds between the atoms of an elastic material.

There are various types of springs identifiable by skilled persons, such as coil springs and torsion springs, that can be used in various implementations of the IOL injectors described herein and within the scope of the present disclosure.

For example, when a helical spring, otherwise known as a coil spring, is compressed or stretched from its resting conformation, it exerts an opposing force approximately proportional to its change in length. The term "resting conformation" as used herein refers to a spring having essentially no stored elastic energy. Coil springs are typically of two types: tension springs or compression springs. Tension or extension springs are designed to become longer under load. Their turns (loops) are typically touching in the unloaded position, and they may have a hook, eye or other means of attachment at each end. In contrast, compression springs are designed to become shorter when loaded. Their turns (loops) are typically not touching in the unloaded position, and they typically need no attachment points such as those used for tension springs.

A torsion spring is a spring that works by torsion or twisting; that is, a flexible elastic object that stores mechanical energy when it is twisted. When it is twisted, it exerts a force, or torque, in the opposite direction, proportional to the amount, or angle, it is twisted.

For example, in some implementations, the spring 1 may be a compression spring 1a, for example as shown in FIG. 8A-FIG. 8D, or a tension spring 1b, for example as shown in FIG. 9A-FIG. 9D, or a torsion spring 1c, for example as shown in FIG. 10A-FIG. 10D.

In some implementations, various combinations of two or more different types of springs may be used in the spring-assisted plunger mechanism described herein, such as a compression spring and a tension spring, and so on.

Other types of springs that may be used in implementations of the spring-assisted plunger mechanism of the present disclosure include, but are not limited to constant springs, variable springs, variable stiffness springs, flat springs, machined springs, serpentine springs, cantilever springs, hollow tubing springs, volute springs, hairsprings, leaf springs, V-springs, Belleville springs, constant-force springs, mainsprings, negator springs, progressive rate coil springs, rubber bands, spring washers, and wave springs, among others identifiable by persons of ordinary skill in the art upon reading the present disclosure.

The spring-assisted plunger mechanism includes a spring-assisted plunger 30a movably coupled within the injector body 20 and aligned within the bore 40. The spring-assisted plunger 30a has a spring 1 having a first end 2 coupled to the plunger body 200 and a second end 3 coupled to the plunger rod 210. The spring-assisted plunger 30a is configured such that, in response to an axial force applied to the plunger body 200, such as an actuation force applied by a user to the plunger body 200 toward the distal end 60 of the injector body 20, the plunger body 200 is adapted to move axially within the injector body 20, and in response, the spring 1 is adapted to store elastic energy. In response to release of stored elastic energy from the spring 1, the plunger rod 210 is adapted to move axially toward the distal end 60 of the injector body.

In some implementations, the spring-assisted plunger 30a is configured such that, in response to a first axial force applied to the plunger body 200, the plunger body 200 may be adapted to move axially from a proximal position to a first distal position. In response, the plunger rod 210 may be adapted to move axially from a first position proximally adjacent to the IOL storage location 80 to a second position proximally adjacent to the IOL dwell position 809 and contact a removable stop 4 adapted to prevent further axial movement of the plunger rod 210. The removable stop 4 may be coupled to the injector body 20. For example, the removable stop 4 may be slidably coupled to the injector body 20, or rotatably coupled to the injector body 20, as described herein. In response to a further axial force applied to the plunger body 200, the plunger body 200 may be adapted to move axially from the first distal position to a second distal position, and in response, the spring 1 is adapted to store elastic energy. In response to removal of the removable stop 4, the plunger rod 210 may be adapted to move axially toward the distal end 60 of the injector body in response to the release of stored elastic energy from the spring 1.

In some implementations, the removable stop may include a pin 4a slidably disposed within a first side of the injector body, such that a first end 5 of the pin 4a is accessible to a user and a second end 6 of the pin 4a is adapted to contact the plunger rod 210. The pin 4a may be adapted such that, in a first configuration, the second end 6 of the pin 4a is adapted to contact the plunger rod 210 and thereby configured to prevent axial movement of the plunger rod 210. In a second configuration, the second end 6 of the pin 4a may be adapted such that it does not prevent axial movement of the plunger rod 210. Accordingly, a user may slide the pin 4a outward, such as in direction of arrow 85 in FIG. 8D, from the first configuration for example as depicted in FIG. 8C such that the pin 4a adopts the second configuration for example as depicted in FIG. 8D.

Figure 11A:
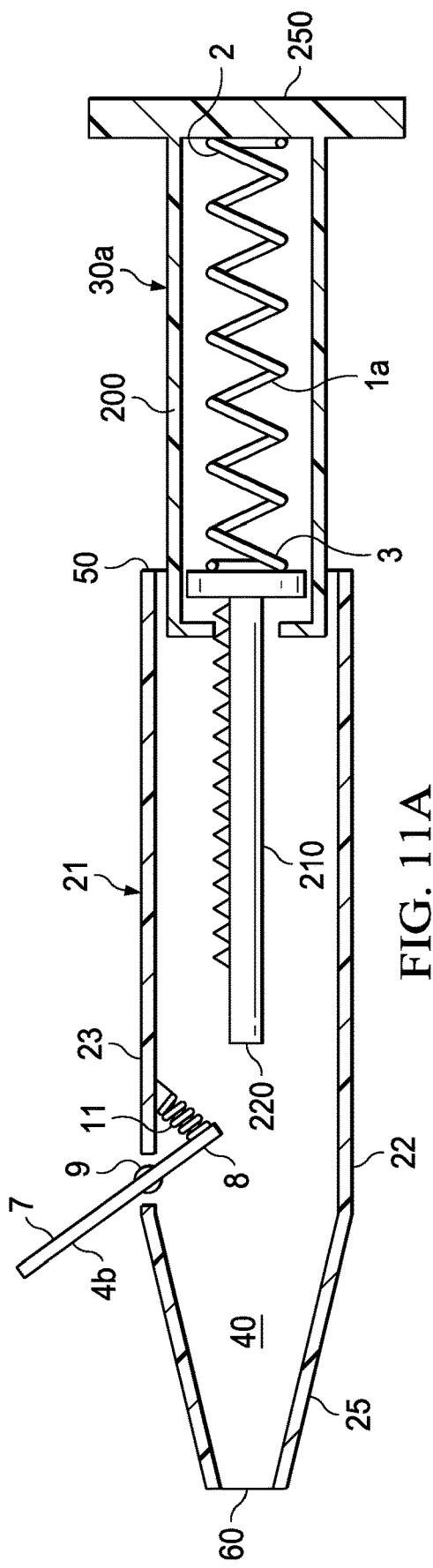
FIG. 11A is a schematic of an example IOL injector having a braking mechanism.
Figure 11B:
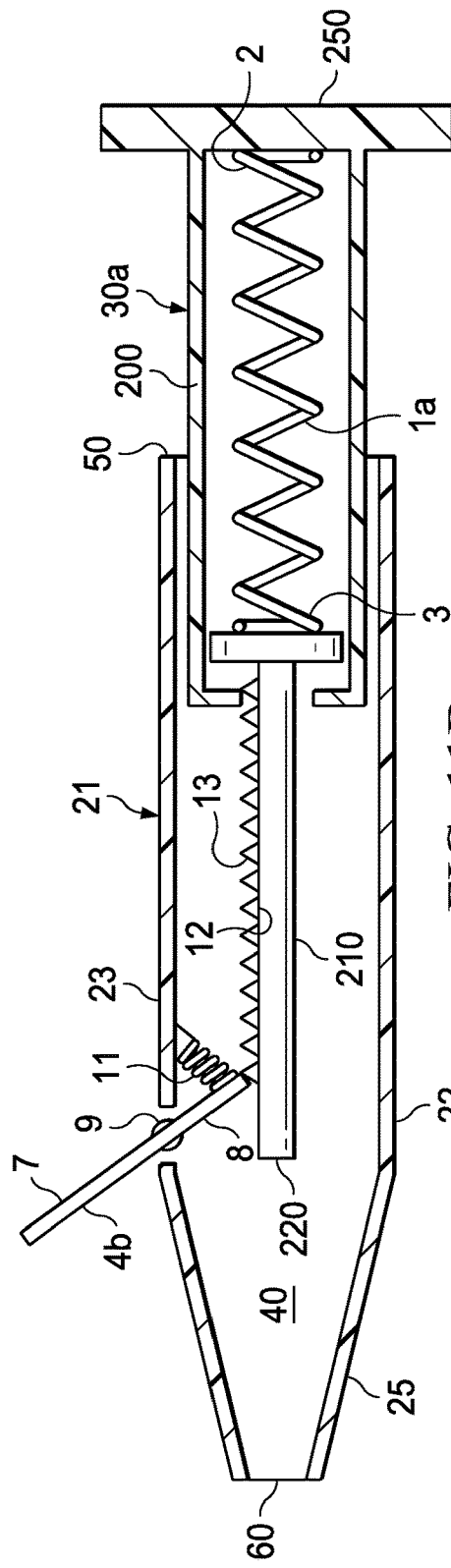
FIG. 11B is another schematic of the example IOL injector of FIG. 11A.
Figure 12C:
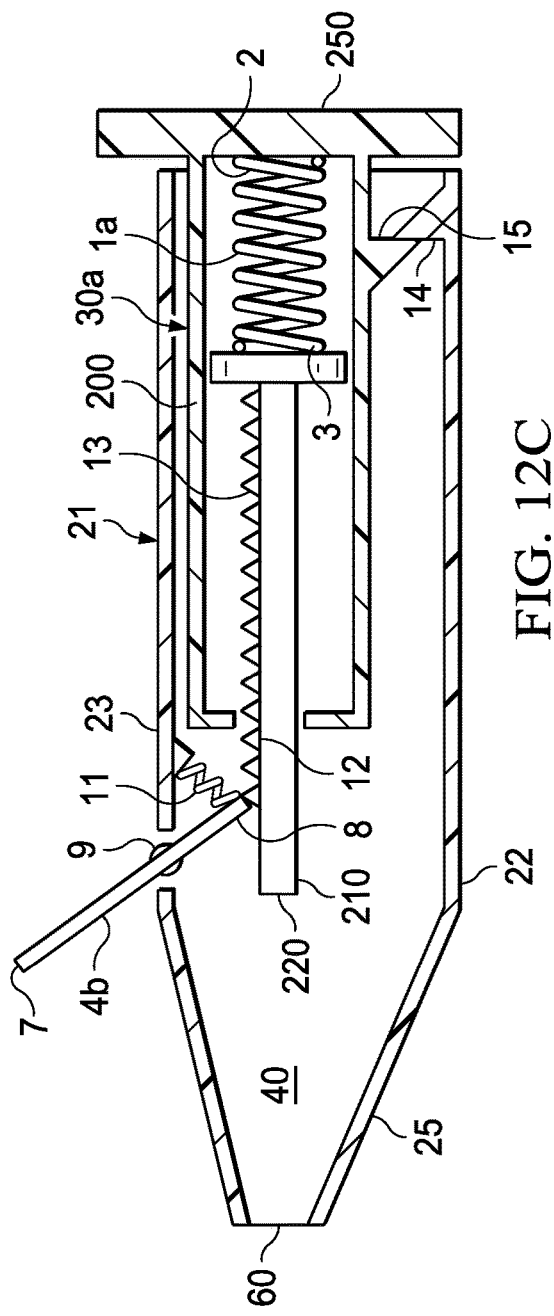
FIG. 12C is yet another schematic of the example IOL injector of FIG. 12A.
Figure 12D:
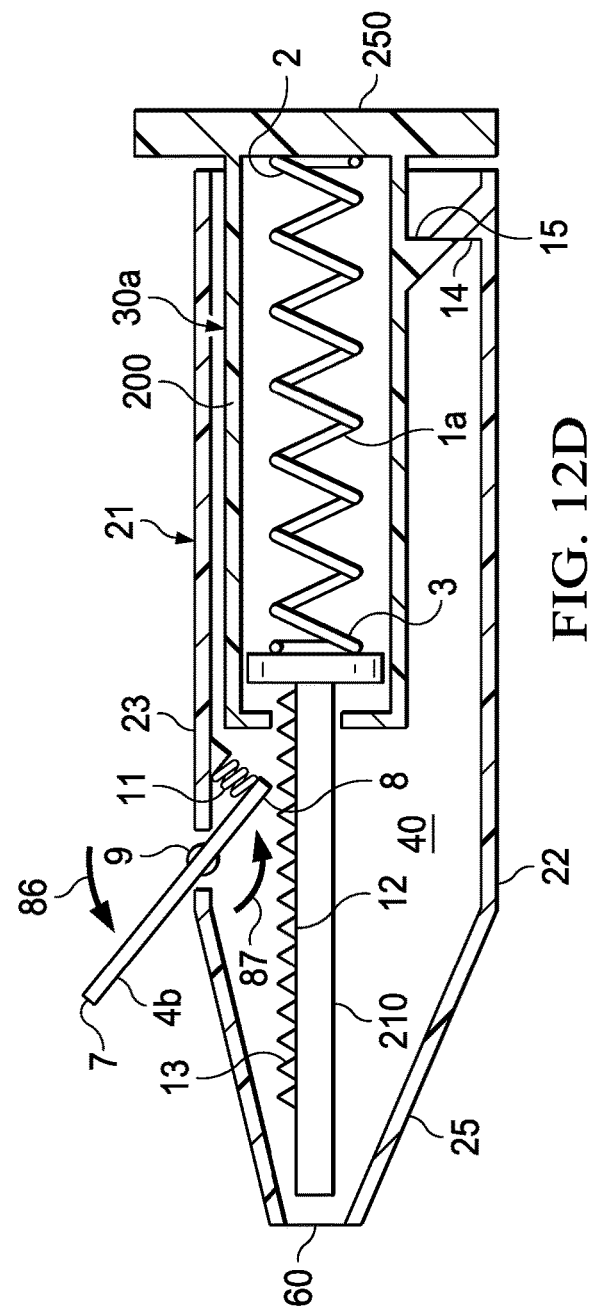
FIG. 12D is still another schematic of the example IOL injector of FIG. 12A.

In some implementations, the removable stop may include a braking mechanism adapted to provide resistance to axial movement of the plunger rod 210. For example, as shown in FIG. 11A-FIG. 11D, the braking mechanism may include a brake lever 4b having a first end that includes a handle 7 accessible to a user and a second end 8 adapted to contact the plunger rod 210 and thereby apply a frictional braking force against axial movement of the plunger rod 210. The brake lever 4b may be coupled to the injector body, such as rotatably coupled at a pivot point 9, disposed between the first and second ends of the brake lever 4b. The braking mechanism may include a brake lever return spring 11 having a first end coupled to the brake lever 4b and a second end coupled to the injector body. The braking mechanism may be adapted such that, in response to a force applied to the handle 7, for example in the direction of arrow 86 as shown in FIG. 11D, such as applied by a finger or a thumb of a user, the second end of the brake lever 4b is adapted to move away from a resting position in contact with the plunger rod 210, for example in the direction of arrow 87 as shown in FIG. 11D, thereby decreasing the frictional braking force. Accordingly, in response to the decreased frictional braking force, the plunger rod 210 is adapted to axially move in response to release of stored elastic energy from the spring 1. The brake lever return spring 11 may be adapted to return the second end of the brake lever 4b to the resting position.

In some implementations, the plunger rod 210 may include a brake pad 12, for example having one or more brake pad ribs 13 adapted to contact the second end 8 of the brake lever 4b, and thereby adapted to apply a frictional braking force against axial movement of the plunger rod 210.

In some implementations, the braking mechanism may be adapted such that the frictional braking force has a value B, the force applied to the handle 7 has a value H, such that B is inversely related to H. Accordingly, in some implementations, a greater force H applied to the handle 7 may result in a faster axial movement of the plunger rod 210. In some implementations, B may be inversely proportional to H. In some implementations, the brake lever 4b may be adapted such that it provides a mechanical advantage. For example, the pivot point 9 may be configured such that a distance between the handle 7 and the pivot point 9 is greater than a distance between the pivot point 9 and the second end adapted to contact the plunger rod 210.

In some implementations, the force applied to the handle 7 has a value H that does not vary as a function of an axial location of the IOL 70 within the nozzle 25, such as a distance of the IOL 70 from the distal end 60 of the nozzle 25. Accordingly, the spring-assisted plunger mechanism may be adapted such that a user can apply a constant or approximately constant amount of force H to the handle 7 in order to advance the IOL through the nozzle 25, such as from the IOL dwell location 809 to the distal end 60 of the nozzle 25. In contrast, as described herein, when axially advancing an IOL through the nozzle of existing IOL injectors having a traditional plunger mechanism, a user typically experiences variable IOL advancement resistance force, and therefore has to apply variable axial force to the plunger to advance the IOL.

In some implementations, the spring-assisted plunger 30a may have a telescoping portion wherein a proximal portion of the plunger rod 210 is coupled, such as concentrically coupled, within a distal portion of the plunger body 200 and axially slidable therein. Accordingly, the spring-assisted plunger 30a may be adapted such that, in response to an axial force applied to the plunger body 200, the proximal portion of the plunger rod 210 is adapted to slidably move within the distal portion of the plunger body 200. In response to release of stored elastic energy from the spring 1, the proximal portion of the plunger rod 210 may be adapted to slidably move within the distal portion of the plunger body 200.

As would be understood by skilled persons, the term "telescoping" generally refers to movement of a first part sliding out from, or into, a second part, where the two parts are coupled, and have an extended or uncollapsed configuration, and a shortened or collapsed configuration. More specifically, the first and second parts may be generally referred to as tubes or cylinders, sometimes referred to as sleeves, having different diameters, wherein a smaller diameter sleeve is coupled concentrically, or nested, within the larger diameter outer sleeve. Two or more concentrically coupled sleeves may form a telescoping cylinder. The movement of one sleeve sliding out from, or into another allows respective lengthening or shortening of the telescoping cylinder. The lengthened, or extended configuration may be referred to as "uncollapsed", and the shortened configuration, for example wherein the length of the smaller diameter tube is entirely or mostly contained within the larger diameter tube may be referred to as "collapsed".

Accordingly, the spring-assisted plunger mechanism may be adapted such that the spring 1 stores elastic energy when the telescoping portion shortens from an uncollapsed configuration to a collapsed configuration and the spring 1 releases elastic energy when the telescoping portion lengthens from a collapsed configuration to an uncollapsed configuration.

In some implementations, for example as shown in FIG. 12A-FIG. 12D, the injector body may include at least one ridge 14 disposed within the bore 40, and the plunger body 200 may include at least one ridge-engaging tooth 15, wherein the at least one ridge 14 and the at least one ridge-engaging tooth 15 are adapted to prevent movement of the plunger body 200 away from the distal end 60 of the injector body of the IOL injector 10. In some implementations, the ridge 14 and the ridge-engaging tooth 15 may be adapted to prevent movement of the plunger body 200 away from the distal end 60 of the injector body of the IOL injector 10 when the plunger body 200 is in the second distal position. Accordingly, the spring 1 may be maintained for a time in a conformation having stored elastic energy as a result of the ridge 14 engaging the ridge-engaging tooth 15, such that the elastic energy is prevented from being released by movement of the plunger body 200 away from the distal end 60 of the injector body 20.

In some implementations, the spring-assisted plunger mechanism may include a damping mechanism configured to provide resistance to axial movement of the plunger rod 210. In particular, in various implementations, the damping mechanism is adapted to control the speed of advancement of the IOL exiting the nozzle 25 of the IOL injector.

For example, such as shown in FIG. 13A-FIG. 13D, the damping mechanism may be a ribbed damping mechanism configured to provide frictional resistance to axial movement of the plunger rod 210. The ribbed damping mechanism may include at least one damping rib 16 disposed on the plunger rod 210 and at least one damping rib 17 disposed within the bore 40. The ribbed damping mechanism may be adapted such that the at least one damping rib 16 on the plunger rod 210 is configured to contact the at least one damping rib 17 disposed within the bore 40 and thereby provides a frictional resistance to axial movement of the plunger rod 210.

In some implementations, the ribbed damping mechanism may be configured to apply an increasing frictional resistance to axial movement of the plunger rod 210 as a function of decreasing distance of the plunger rod 210 from the distal end 60 of the nozzle 25. For example, in some implementations, the at least one damping rib 16 on the plunger rod 210 and/or the at least one damping rib 17 disposed within the bore 40 may include a plurality of damping ribs 16/17, and a distance between each of the damping ribs 16/17 decreases with decreasing distance from the distal end 60 of the nozzle 25. In some implementations, the at least one damping rib 16 on the plunger rod 210 and/or the at least one damping rib 17 disposed within the bore 40 may include a plurality of damping ribs 16/17, and a number of damping ribs 16 on the plunger rod 210 contacting a number of damping ribs 17 disposed within the bore 40 increases with decreasing distance from the distal end 60 of the nozzle 25.

Figure 14A:
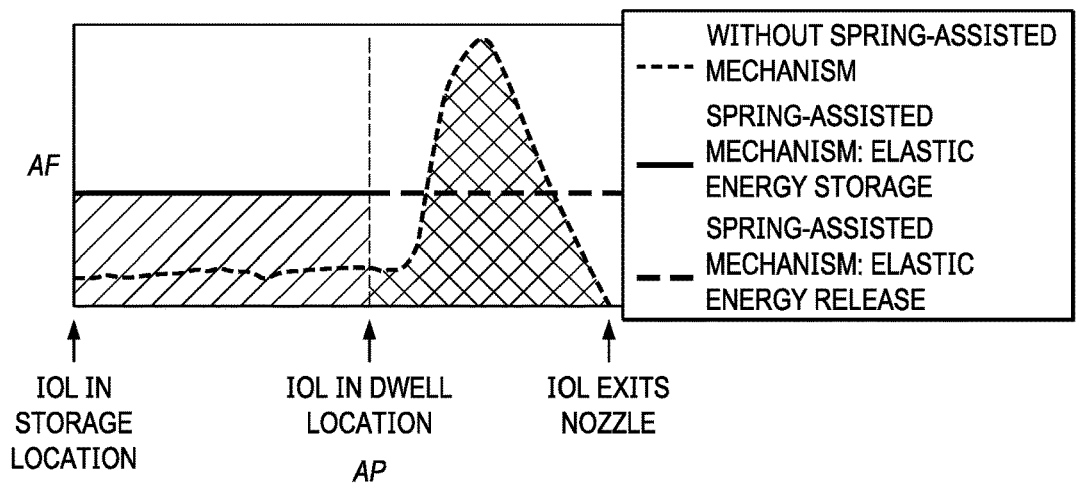
FIG. 14A is a graph showing example simulated IOL injection force profiles.
Figure 14B:
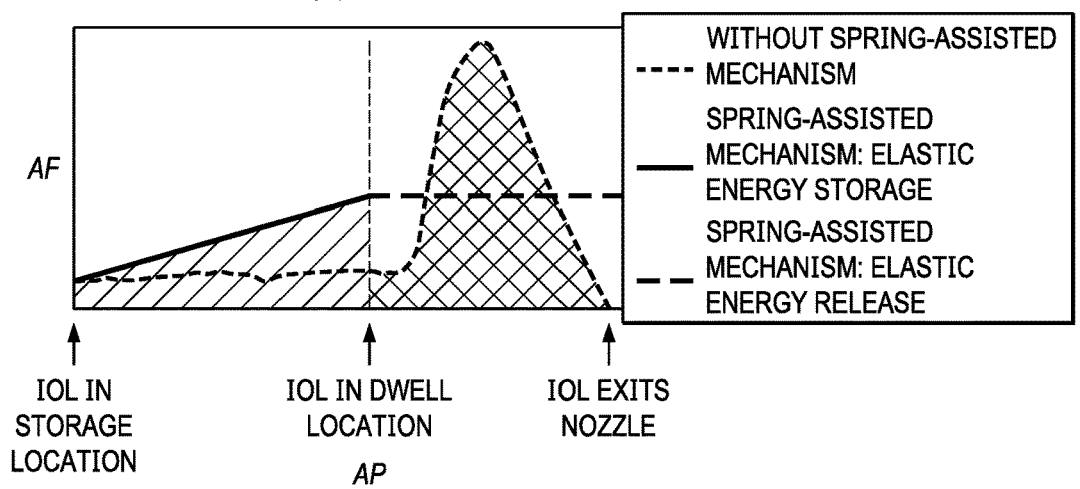
FIG. 14B is another graph showing example simulated IOL injection force profiles.
Figure 14C:
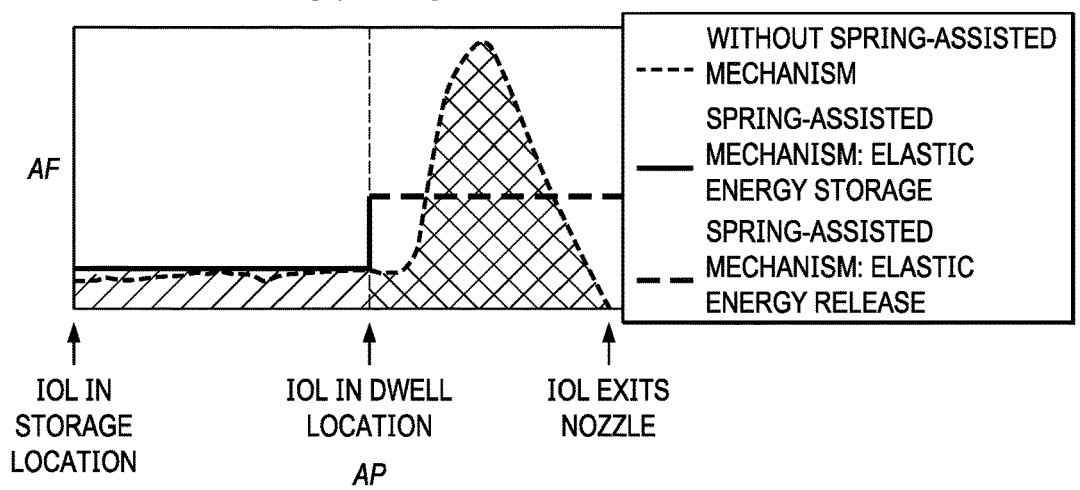
FIG. 14C is yet another graph showing example simulated IOL injection force profiles.

FIG. 14A-FIG. 14C are graphs showing example simulated IOL injection force profiles. Without limitation to theory, it will be understood that an IOL injector has an IOL injection force profile, which refers herein to a relationship between an axial location of an IOL within the bore (AP), and a force applied, such as by a user, to axially move an IOL within the bore (AF), such as force required to overcome an IOL advancement resistance.

In the example graphs of FIG. 14A-FIG. 14C, the horizontal axis of the graphs, labeled AP, indicates the axial location of an IOL within the bore (AP), for example shown as beginning at the IOL storage location at the left end of the horizontal axis, and ending at the right end of the horizontal axis at the location where the IOL exits the nozzle. The graphs of FIG. 14A-FIG. 14C show a vertical dashed line that indicates the IOL dwell location, intersecting the horizontal axis between the IOL storage location and the exit of the nozzle. A numerical value for AP may be, for example, distance from the IOL storage location, for example in mm. The vertical axis, labeled AF, represents the force applied by a user to axially move an IOL within the bore, such as force required to overcome an IOL advancement resistance in order to axially advance the IOL through the bore. A numerical value for AF may be, for example, in Nm. In some implementations, the AF may refer to the force applied by a user to axially advance the plunger, for example a force applied to the plunger body, or a force applied to the handle of the braking mechanism, as described herein.

In FIG. 14A-FIG. 14C, the charted line labeled "without spring-assisted mechanism" shows an example of an injection force profile of a typical existing, traditionally manually actuated IOL injector that does not have a spring-assisted plunger mechanism described herein. For example, in typical existing IOL injectors, the AF associated with advancing the IOL from the IOL storage location to IOL dwell location is typically low; after reaching the IOL dwell location, further axial advancement of the IOL is associated with an increase in AF up to where the IOL is maximally compressed within the nozzle, followed by a rapid decrease in AF as the IOL exits the nozzle.

In various implementations described herein, an IOL injector having a spring-assisted plunger mechanism is configured to have a force profile having minimal variability of AF as a function of AP. An IOL injector having a spring-assisted plunger mechanism described herein is configured to have a force profile having decreased variability of AF as a function of AP compared with typical existing IOL injectors that do not have the spring-assisted plunger mechanism described herein.

In various implementations, an IOL injector having a spring-assisted plunger mechanism described herein may have an increased AF associated with storage of elastic energy, such as during advancement of the IOL from the IOL dwell location to the exit of the nozzle. For example, such as in FIG. 14A, the spring-assisted mechanism may be adapted to have an increased AF during movement of the IOL from the IOL storage location to the IOL dwell location; the force profile for the spring-assisted mechanism during the phase of elastic energy storage in FIG. 14A is shown as being relatively flat, such as having a slope having a value at or near zero, associated with a relatively constant elastic energy storage during plunger body advancement as the IOL moves axially from the IOL storage location to the IOL dwell location. In other implementations, such as depicted in FIG. 14B, the spring-assisted mechanism may be adapted such that the value of AF may increase as the plunger is advanced from the IOL storage location to the IOL dwell location. In yet another implementation of the spring-assisted mechanism, such as depicted in FIG. 14C, the value of AF may be relatively low as the IOL is advanced from the IOL storage location to the IOL dwell location, without substantial elastic energy storage during this phase, and then, for example, upon engagement of the plunger rod with the removable stop, the value of AF increases as the plunger body 200 is further advanced to store elastic energy, while the plunger tip 220 and the IOL 70 remain at the IOL dwell location.

The spring-assisted mechanism described herein in various implementations may have linear, progressive, or variable rate springs, among others identifiable by skilled persons upon reading the present disclosure and may therefore be adapted to have a force profile during elastic energy storage such as those depicted in FIG. 14A-FIG. 14C.

Also, in contrast with the AF of traditional IOL injectors, an IOL injector having the spring-associated plunger mechanism described herein may have decreased variability of AF during advancement of the IOL from the IOL dwell location to the exit of the nozzle, associated with the release of elastic energy to advance the IOL from the IOL dwell location to the exit of the nozzle. For example, the spring-assisted plunger mechanism may have decreased variability of AF as the IOL advances from the IOL dwell location following removal of the removable stop, such as associated in some implementations with depression of the handle of the braking mechanism to advance the IOL from the dwell location until the IOL exits the nozzle. In some implementations, the spring-assisted plunger mechanism has decreased AF as the IOL becomes more compressed within the nozzle, as the release of elastic energy provides an axial driving force in opposition to the IOL advancement resistance. In some implementations, the damping mechanism may also provide a resistive force in opposition to IOL advancement, adapted to prevent sudden release of pressure of the IOL as the IOL exits nozzle.

In some implementations, an IOL injector having a spring-assisted plunger mechanism described herein is configured to have a force profile having minimal variability of AF as a function of AP as an IOL is advanced from an IOL dwell location 809 to the exit of the nozzle 25. For example, the slope of the line indicating "spring-assisted mechanism: elastic energy release" in the graphs of FIG. 14A-FIG. 14C has a slope at or near zero as an IOL is advanced from an IOL dwell location 809 to the exit of the nozzle 25. In contrast, the line indicating C"without spring-assisted mechanism has a more variable slope, having a positive slope value up to the point of maximal IOL compression, followed by a negative slope value to the point where the IOL exits the nozzle. Accordingly, an IOL injector having the spring-assisted plunger mechanism of the present disclosure does not have the large increase in AF as the IOL is maximally compressed, and also does not have the rapid decrease in AF as the IOL exits the nozzle.

Thus, in implementations of the spring-assisted plunger mechanism of the present disclosure, by harnessing elastic energy while the plunger body is advanced during the elastic energy storage phase and subsequently using the elastic energy for plunger rod advancement during the elastic energy release phase, and optionally also slowing plunger rod advancement as the IOL exits the nozzle utilizing the damping mechanism described herein, the spring-assisted plunger mechanism solves the problems associated with some existing IOL injectors that have the variable IOL advancement force profile having peak and trough AF.

In various implementations of the spring-assisted plunger mechanism of the present disclosure, the release of stored elastic energy provides a driving force to axially move the plunger rod 210 through the bore 40 of the IOL injector towards the distal end of the IOL injector body 20. In contrast to some existing IOL injectors in which elastic energy is "pre-stored" before receipt of the IOL injector by a user, the spring-assisted mechanism of the present disclosure is adapted such that elastic energy is stored in response to advancement of the plunger by the user, such as just prior to delivery of the IOL to an eye of a patient. In some cases, "pre-stored" IOL injectors may have safety risks, or may have increased risk of mechanical failure, when elastic energy is stored before receipt of the IOL injector by the user. Therefore, the spring-assisted mechanism of the present disclosure may have advantages of increased safety and/or mechanical stability of the IOL injector, by avoiding having a "pre-stored" spring mechanism having elastic energy stored during storage, before use of the IOL injector by a user.

In various implementations described herein, the spring-assisted mechanism of the present disclosure may be considered a hybrid of a manual and automatic IOL advancement mechanism, wherein elastic energy is stored by manual actuation of the plunger by a user, followed by axial movement of the plunger driven, either fully automatically in response to release of stored energy from a spring, or partially in response to release of stored energy from a spring combined with force applied by a user.

In some implementations, during the release of elastic energy from the spring, plunger advancement may occur automatically, in absence of actuation by a user, for example in absence of an axial force applied to the plunger by a user. Thus, in some implementations, in response to removal of the removable stop, the release of elastic energy may automatically drive axial plunger advancement. In some implementations described herein, a braking mechanism may be included in the IOL injector, wherein a user may release application of a braking force on the plunger to allow release of the stored energy from the spring to automatically drive axial movement of the plunger.

In other implementations, the spring-assisted plunger mechanism may be adapted such that the release of elastic energy in the spring-assisted plunger mechanism is not configured to automatically axially drive IOL advancement, but instead, for example, may provide a lower level or partial axial driving force to assist a user to advance the IOL, such that the IOL is advanced by user application of force to actuate plunger advancement, but the user is not required to apply as much axial force as would be necessary in absence of the elastic energy release of the spring-assisted plunger mechanism, such as in traditional fully manually actuated IOL injectors. Accordingly, in some implementations, the release of stored elastic energy may assist IOL advancement and may provide a less variable experience of AF for the user.

Accordingly, in some implementations, the spring may be selected for use in the spring-assisted mechanism of the present disclosure such that the spring has the desired level of potential elastic energy storage for either an automatic axial driving force (a high level of elastic energy storage, such as a spring adapted to have greater than, or have greater than about, 0.875 Nm of force storage), or a partial assistive axial driving force (a lower level of elastic energy storage, such as a spring adapted to have less than, or have less than about, 0.875 Nm of force storage). In some implementations, an axial driving force of a spring adapted to provide either an automatic driving force or a partial assistive driving force may be calculated with reference to a peak IOL advancement resistance force of an IOL within an IOL injector, and a distance between the dwell location and the exit of the nozzle. For example, in some IOL injectors, a peak IOL advancement resistance force may be, or be about, 35 N and the distance between the dwell location and the exit of the nozzle may be, or be about 0.025 m. Accordingly, therefore, for example, in some implementations, the spring may be selected having potential elastic storage equal to, greater than, or less than 35 N*0.025 m=0.875 Nm or thereabouts.

In some implementations, the spring-assisted plunger mechanism of the present disclosure may be adapted to separately inject an IOL base 461, an IOL optic 460, or both. In some implementations, the spring-assisted plunger mechanism of the present disclosure may be adapted to concurrently inject an IOL base 461 and an IOL optic 460.

Non-limiting examples of IOL injectors that may be adapted according to the present disclosure include those described in U.S. Pat. No. 7,156,854 and U.S. Patent Application Publication No. 2016/0256316, the disclosures of each being incorporated herein by reference in their entireties.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. An intraocular lens (IOL) injector comprising: an injector body having: a main body having a proximal end and a distal end; a nozzle having a proximal end and a distal end, the proximal end of the nozzle coupled to the distal end of the main body, the nozzle further comprising an IOL storage location configured to house an IOL, and an IOL dwell location distal to the IOL storage location; a bore having a longitudinal axis extending from the proximal end of the main body to the distal end of the nozzle; a spring-assisted plunger movably coupled within the injector body and aligned within the bore, the plunger having: a plunger body having a proximal end accessible to a user and a distal end; a plunger rod having a proximal end and a distal end; a plunger tip formed at the distal end of the plunger rod and adapted to contact an IOL and axially move the IOL in response to an axial force applied to the plunger; and a spring having a first end coupled to the plunger body and a second end coupled to the plunger rod; wherein in response to an axial force applied to the plunger body: the plunger body is adapted to move axially, and in response, the spring is adapted to store elastic energy; the plunger rod is adapted to move axially from a first position proximally adjacent to the IOL storage location to a second position proximally adjacent to the IOL dwell position and contact a removable stop adapted to prevent further axial movement of the plunger rod, the removable stop coupled to the injector body; and wherein, in response to the removal of the removable stop and the release of stored elastic energy from the spring, the plunger rod is adapted to move axially toward the distal end of the injector body.

2. The IOL injector of claim 1, wherein: the removable stop comprises a pin slidably disposed within a first side of the injector body; wherein: a first end of the pin is accessible to the user; and a second end of the pin is adapted to contact the plunger rod; wherein: in a first configuration, the second end of the pin is adapted to contact the plunger rod and configured to prevent axial movement of the plunger rod; and in a second configuration, the second end of the pin is adapted not to prevent axial movement of the plunger rod.

3. The IOL injector of claim 1, wherein: the removable stop comprises a braking mechanism adapted to provide resistance to axial movement of the plunger rod, the braking mechanism having; a brake lever having a first end comprising a handle accessible to the user and a second end adapted to contact the plunger rod and thereby apply a frictional braking force against axial movement of the plunger rod; the brake lever coupled to the injector body at a pivot point disposed between the first and second ends of the brake lever; and a brake lever return spring having a first end coupled to the brake lever and a second end coupled to the injector body; wherein in response to a force applied to the handle; the second end of the brake lever is adapted to move away from a resting position in contact with the plunger rod, thereby decreasing the frictional braking force; in response to the decreased frictional braking force, the plunger rod is adapted to axially move in response to release of stored elastic energy from the spring; and the brake lever return spring is adapted to return the second end of the brake lever to the resting position.

4. The IOL injector of claim 3, wherein: the plunger rod comprises a brake pad having one or more brake pad ribs adapted to contact the second end of the brake lever, and thereby apply the frictional braking force against axial movement of the plunger rod.

5. The IOL injector of claim 3, wherein:
the frictional braking force has a value B;
the force applied to the handle has a value H; and
B is inversely related to H.

6. The IOL injector of claim 1, wherein: the injector body further comprises at least one ridge disposed within the bore; and the plunger body further comprises at least one ridge-engaging tooth; wherein the at least one ridge and the at least one ridge-engaging tooth are adapted to prevent movement of the plunger body away from the distal end of the injector body of the IOL injector.

7. The IOL injector of claim 6, wherein the at least one ridge and the at least one ridge-engaging tooth are adapted to prevent movement of the plunger body away from the distal end of the injector body of the IOL injector when the plunger body is in a second distal position.

8. The IOL injector of claim 1, further comprising: a ribbed damping mechanism configured to provide frictional resistance to axial movement of the plunger rod, the ribbed damping mechanism comprising: at least one damping rib disposed on the plunger rod and at least one damping rib disposed within the bore; wherein the at least one damping rib on the plunger rod is configured to contact the at least one damping rib disposed within the bore and adapted to provide frictional resistance to axial movement of the plunger rod.

9. The IOL injector of claim 8, wherein:
the ribbed damping mechanism is configured to apply an increasing frictional resistance to axial movement of the plunger rod as a function of decreasing distance of the plunger rod from the distal end of the nozzle.

10. The IOL injector of claim 9, wherein:
the at least one damping rib on the plunger rod and/or the at least one damping rib disposed within the bore comprises a plurality of damping ribs; and
a distance between each of the damping ribs decreases with decreasing distance from the distal end of the nozzle.

11. The IOL injector of claim 8, wherein: the IOL injector has an IOL injection force profile comprising a relationship between an axial location of the IOL within the bore (AR) and a force applied by the user to axially move the IOL within the bore (AF); wherein the IOL injector is configured to have a force profile having minimal variability of AF as a function of AR.

12. The IOL injector of claim 9, wherein:
the at least one damping rib on the plunger rod and/or the at least one damping rib disposed within the bore comprises a plurality of damping ribs; and
a number of damping ribs on the plunger rod contacting a number of damping ribs disposed within the bore increases with decreasing distance from the distal end of the nozzle.

13. The IOL injector of claim 1, wherein:
the spring is a compression spring, a tension spring, or a torsion spring.

14. The IOL injector of claim 1, wherein: the plunger has a telescoping portion wherein a proximal portion of the plunger rod is concentrically coupled within a distal portion of the plunger body, and axially slidable therein, wherein: in response to the axial force applied to the plunger body, the proximal portion of the plunger rod is adapted to slidably move within the distal portion of the plunger body; and in response to release of stored elastic energy from the spring, the proximal portion of the plunger rod is adapted to slidably move within the distal portion of the plunger body.

15. The IOL injector of claim 1, wherein:
the IOL injector is adapted to separately inject an IOL base, an IOL optic, or both.

16. The IOL injector 10 of claim 1, wherein:
the IOL injector is adapted to concurrently inject an IOL base and an IOL optic.

* * * * *